United States Patent [19]

Matsumura et al.

[11] Patent Number: 5,120,733
[45] Date of Patent: Jun. 9, 1992

[54] CARBAMOYLPYRROLIDONE DERIVATIVES AND DRUGS FOR SENILE DEMENTIA

[75] Inventors: Hiromu Matsumura; Toshisada Yano; Akira Matsushita, all of Hyogo; Masami Eigyo, Nara, all of Japan

[73] Assignee: Shionogi and Co. Ltd., Osaka, Japan

[21] Appl. No.: 571,402

[22] Filed: Aug. 23, 1990

Related U.S. Application Data

[62] Division of Ser. No. 233,142, Aug. 17, 1988, Pat. No. 4,977,167.

[30] Foreign Application Priority Data

Aug. 19, 1987 [JP] Japan .................... 62-205956

[51] Int. Cl.$^5$ ............... A61K 31/495; C07D 401/14; C07D 403/14
[52] U.S. Cl. .................... 514/252; 544/295; 544/316; 544/360; 544/364; 544/372; 546/20; 546/208; 546/209; 546/280; 546/281; 548/136; 548/171; 548/187; 548/246; 548/302; 548/336; 548/374; 548/538; 548/267.6
[58] Field of Search ............... 514/252; 544/295, 360, 544/372

[56] References Cited

U.S. PATENT DOCUMENTS

| | | | |
|---|---|---|---|
| 2,829,146 | 4/1958 | Beaver et al. | 548/539 |
| 4,118,396 | 10/1978 | Pifferi et al. | 544/372 |
| 4,369,139 | 1/1983 | Kyburz et al. | 548/539 |

FOREIGN PATENT DOCUMENTS 0089900 3/1983 European Pat. Off. .

OTHER PUBLICATIONS

Chemical Abstracts, vol. 87, No. 17, p. 217, Abstract No. 87:128886g.
Chemical Abstracts, vol. 91, No. 4, p. 611, Abstract No. 91:39238n.
Chemical Abstracts, vol. 95, No. 19, p. 719, Abstract No. 95:168964c.

*Primary Examiner*—C. Warren Ivy
*Assistant Examiner*—James H. Turnipseed
*Attorney, Agent, or Firm*—Birch, Stewart, Kolasch & Birch

[57] ABSTRACT

A compound of the formula:

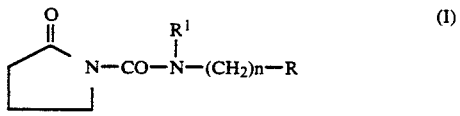

(wherein R is phenoxy optionally substituted by a halogen, methoxy, or methyl group,

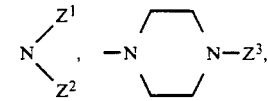

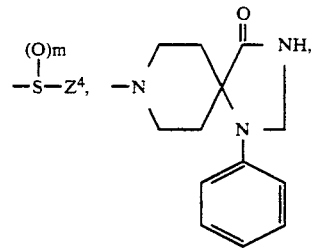

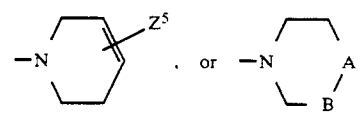

one of A and B is

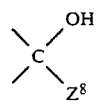

and the other is >CH$_2$;

R$^1$ is hydrogen or C$_1$–C$_5$ alkyl;
Z$^1$ is phenyl, benzyl, or isoxazolyl each optionally substituted by a halogen, methoxy, or methyl group; Z$^2$ is hydrogen, C$_1$–C$_5$ alkyl, C$_2$–C$_5$ alkenyl, or phenyl optionally mono-, di-, or tri-substituted by a halogen, methoxy, or methyl group; or Z$^1$ and Z$^2$ taken together with the adjacent nitrogen atom may form 5-membered heterocyclic group; Z$^3$ is C$_1$–C$_5$ hydroxyalkyl, di(C$_1$–C$_5$ alkyl) sulfamoyl, 6-membered heterocyclic group, phenyl, benzyl, or phenylsulfonyl each phenyl moiety of the last three members being optionally substituted by a halogen, methoxy, or methyl group; Z$^4$ is phenyl optionally substituted by a halogen, methoxy, or methyl group or 5- or 6-membered heterocyclic group which is optionally substituted by a halogen, methoxy, or methyl group and which can be optionally condensed with a benzene ring; Z$^5$ is thienyl or phenyl each optionally substituted by a halogen, methoxy, or methyl group; Z$^6$ is thienyl or phenyl each optionally substituted by a halogen, methoxy, or methyl group; m is an integer from 0 to 2; n is an integer from 2 to 3)

or its pharmaceutical acceptable acid addition salt being useful as a drug for senile dementia, psychotropic, or antiamnesia agent is provided through several routes.

3 Claims, No Drawings

CARBAMOYLPYRROLIDONE DERIVATIVES AND DRUGS FOR SENILE DEMENTIA

This application is a divisional of copending application Ser. No. 07/233,142, filed on Aug. 17, 1988, now U.S. Pat. No. 4,977,167.

This invention relates to carbamoylpyrrolidone derivatives. More particularly, this invention is directed to carbamoylpyrrolidone derivatives which have been found to be particularly available as a drug for senile dementia, psychotropic, and/or antiamnesia agents, to their preparation, to their use and to pharmaceutical formulations containing the compounds.

Pyrrolidone derivatives have heretofore been known as the drugs for brain insufficiency disease and so on, for example, in EP Pat. Publn. No. 89900-B, in U.S. Pat. No. 4,369,139, and in U.S. Pat. No. 4,118,396.

The inventors of the present invention have been studying antiamnesia agents of the pyrrolidone family including such compounds. Thus, the present invention has been established, where compounds of the present invention can be applicable for treating some kinds of senile dementia.

SUMMARY OF THE INVENTION

According to the present invention, there is provided a carbamoylpyrrolidone derivative of the formula:

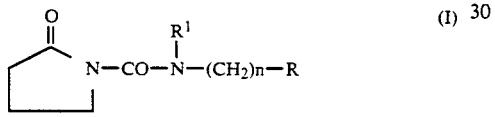

(wherein R is phenoxy optionally substituted by a halogen, methoxy, or methyl group,

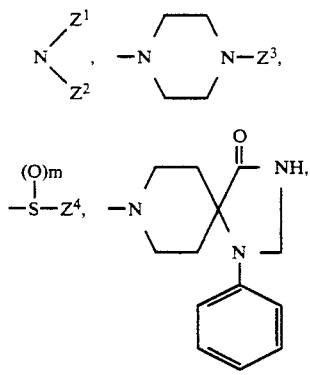

one of A and B is

and the other is $>CH_2$;

$R^1$ is hydrogen or $C_1$-$C_5$ alkyl; $Z^1$ is phenyl, benzyl, or isoxazolyl each optionally substituted by a halogen, methoxy, or methyl group; $Z^2$ is hydrogen, $C_1$-$C_5$ alkyl, $C_2$-$C_5$ alkenyl, or phenyl optionally mono-, di-, or tri-substituted by a halogen, methoxy, or methyl group; or $Z^1$ and $Z^2$ taken together with the adjacent nitrogen atom may form 5-membered heterocyclic group; $Z^3$ is $C_1$-$C_5$ hydroxyalkyl, di($C_1$-$C_5$ alkyl)sulfamoyl, 6-membered heterocyclic group, phenyl, benzyl, or phenylsulfonyl each phenyl moiety of the last three members being optionally substituted by a halogen, methoxy, or methyl group; $Z^4$ is phenyl optionally substituted by a halogen, methoxy, or methyl group or 5- or 6-membered heterocyclic group which is optionally substituted by a halogen, methoxy, or methyl group and which can be optionally condensed with a benzene ring; $Z^5$ is thienyl or phenyl each optionally substituted by a halogen, methoxy, or methyl group; $Z^6$ is thienyl or phenyl each optionally substituted by a halogen, methoxy, or methyl group; m is an integer from 0 to 2; n is an integer from 2 to 3) or its pharmaceutical acceptable acid addition salt.

The terms used in the above definition are explained below.

As the alkyl, methyl, ethyl, propyl, isopropyl, butyl, and pentyl are exemplified. As the alkoxy, methoxy, ethoxy, propoxy, isopropoxy, butoxy, and pentyloxy are exemplified. As the hydroxyalkyl, hydroxymethyl, hydroxyethyl, and hydroxybutyl are exemplified. As the dialkylsulfamoyl, dimethylsulfamoyl, diethylsulfamoyl, and dibutylsulfamoyl are exemplified. As the halogen, fluorine, chlorine, bromine, and iodine are indicated. As the 5- or 6-membered heterocyclic group, isothiazolyl, pyrazolyl, pyrimidinyl, triazolyl, thiadiazolyl, imidazolyl, isoxazolyl, and pyridyl are illustrated.

The processes of producing Compound (I) are shown in the following scheme.

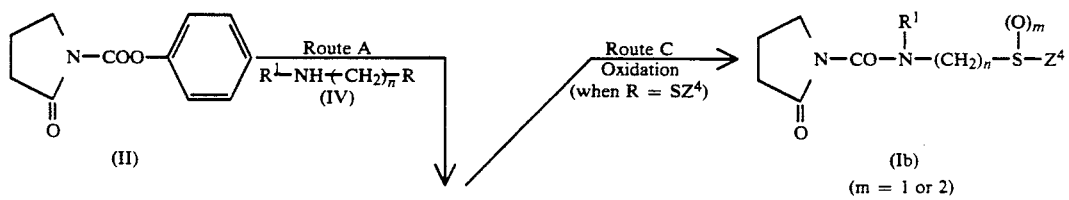

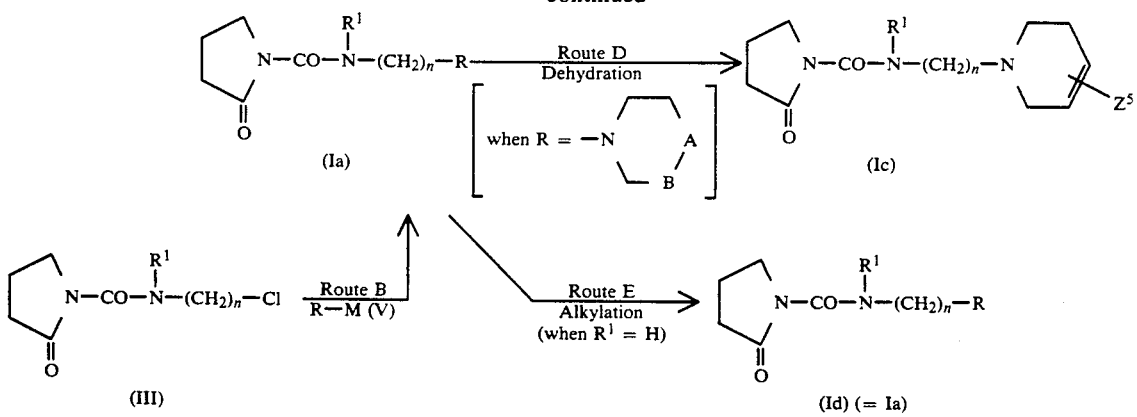

ROUTE A

Compound (Ia) is obtained by reacting Compound (II) with a reagent (IV). In this reaction, no solvent is used and the reaction is carried out at comparatively high temperature of 100°–150° C., preferably at 115°–125° C. As the reagent (IV), 2-(4-methoxyphenylamino)ethylamine, 2-(4-methylphenylamino)ethylamine, 2-(4-chlorophenylamino)ethylamine, 1-aminoethylpyrazole, 2-(4-methoxyphenylamino)-N-methylethylamine, 2-(4-methoxyphenyloxy)-N-methylethylamine, 2-(4-methoxyphenyloxy)ethylamine, and 2-(5-methylisoxazol-3-ylamino)ethylamine are exemplified.

ROUTE B

The object compound (Ia) is obtained by reacting Compound (III) with Compound (V). The reaction is carried out in an appropriate solvent at 10°–120° C., preferably at 50°–100° C. As the solvent, benzene, dimethyl sulfoxide, DMF, chloroform, ethyl acetate, and THF are illustrated. If necessary, organic bases such as pyridine, triethylamine, and dimethylaniline; or inorganic bases such as $K_2CO_3$, NaH, and NaOH may be added as dehydrohalogenating agents. Also an alkali metal iodide such as NaI and KI may be used to accelerate the reaction.

ROUTE C

Compound (Ib) can be obtained by oxidizing Compound (Ia) (when $R=SZ^4$) with a suitable peracid. Generally, this reaction is carried out in an appropriate solvent at room temperature (1°–30° C.), preferably at 10°–25° C. As the solvent, there are chloroform, $CH_2Cl_2$, carbon tetrachloride, ethyl acetate, and 1,2-dichloroethane, or a mixture of some of these solvents. As the peracid, peracetic acid, perbenzoic acid, and m-chloroperbenzoic acid (m-CPBA) are used.

ROUTE D

Compound (Ic) is obtained by subjecting Compound (Ia) to dehydration reaction, when R is

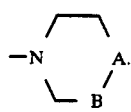

This reaction is carried out in an appropriate solvent in the presence of dehydrating agents at the refluxing temperature of the solvent. As the solvent, toluene, dioxane, hexamethylphosphoramide, and ethyl acetate are exemplified. As the dehydrating agent, phosphorus pentoxide, DCC, and Molecular Sieves are illustrated.

ROUTE E

Compound (Id) is obtained by alkylating Compound (Ia) (when $R^1=H$) with a suitable alkylating agent. Generally, this reaction is carried out in an appropriate solvent at room temperature (1°–30° C.), preferably at 10°–25° C. As the solvent, THF and ethyl acetate are illustrated. As the alkylating agent, methyl iodide, ethyl iodide, butyl chloride, and allyl bromide are exemplified. In order to accelerate the reaction, a suitable base may be used. As the base, alkali metal hydroxide such as sodium hydroxide and potassium hydroxide; potassium hydrogencarbonate, pyridine, triethylamine are exemplified.

The production of the starting materials (II) and (III) are shown in the following scheme.

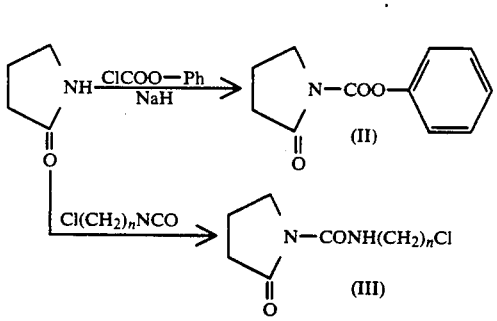

(n is an integer of 2 or 3) (See Referential Examples 1–3)

The compounds (I) may be manufactured by any of the conventional processes known in the chemical literature for the manufacture of analogous compounds.

The compound (I) can be converted into its pharmaceutically acceptable acid addition salt. Such acids illustratively include inorganic acids such as hydrochloric acid, sulfuric acid, phosphoric acid, nitric acid, hydrobromic acid, and hydrogen iodide and organic acids such as acetic acid, maleic acid, malic acid, citric acid, lactic acid, succinic acid, and methanesulfonic acid.

The objective compound (I) of this invention can be administered to humans or animals orally or parenterally. For instance, Compound (I) can be administered orally in the forms of tablets, granules, powder, capsules, solution, etc., or it is given parenterally in the forms of injection or suppositories. These preparations are manufactured in a known process by using additives such as diluents, binders, disintegrators, lubricants, stabilizers, corrigents, suspenders, dispersants, solubilizers, and antiseptics.

As the diluents, lactose, sucrose, starch, cellulose, and sorbit; as the binders, gum arabic, gelatin, and polyvinylpyrrolidone; and as the lubricants, magnesium stearate, talc, and silica gel are exemplified, respectively. When the objective compound (I) of this invention is used for the treatment of senile dementia, a daily dose of about 0.01 to 20 mg/kg may be orally or parenterally administered once or in several divisions.

Embodiments of this invention are illustrated below by indicating Examples, Referential Examples, and Preparations.

The abbreviations used in the Examples, Referential Examples and Tables have the following meanings as mentioned below:

DMF: N,N-Dimethylformamide
m-CPBA: m-Chloroperbenzoic acid
THF: Tetrahydrofuran
EtI: Ethyl iodide
Et$_2$O: Ether
Me: Methyl
Et: Ethyl
MeO: Methoxy
EtOH: Ethanol
i-PrOH: Isopropanol
MeOH: Methanol
DMA: N,N-Dimethylacetamide
hr.: hour
d.: day

EXAMPLE 1

1-[[2-(4-Methoxyphenyl)aminoethyl]carbamoyl]-2-oxopyrrolidine (Ia-1)

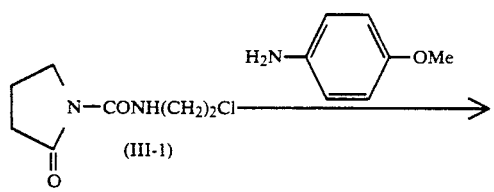

-continued

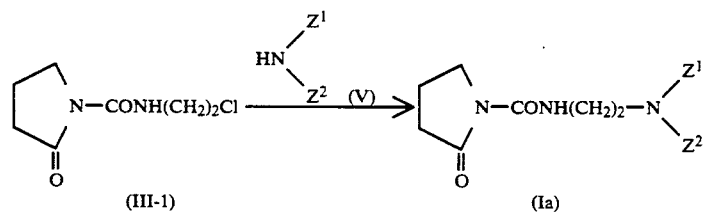

To a solution of 1.0 g (5.24 mmol) of 1-[(2-chloroethyl)carbamoyl]-2-oxopyrrolidine and 0.646 g (5.24 mmol) of p-anisidine in 15 ml of DMF were added 1.09 g (7.86 mmol) of $K_2CO_3$ and 0.30 g (2.00 mmol) of NaI, and the solution was heated with stirring at 80°–85° C. for 40.5 hr. The reaction solution was mixed with ethyl acetate, washed with water, dried, and concentrated. The residue was refined by silica gel chromatography, and 0.37 g (Yield 25.4%) of the objective compound (Ia-1) was obtained from the eluate with benzene-ethyl acetate (3/1 v/v). The product obtained was washed with ether-n-hexane and collected by filtration.

m.p.: 83.5°–84.5° C.

Anal. Calcd. (%) for $C_{14}H_{19}N_3O_3$: C, 60.63; H, 6.91; N, 15.15

Found (%): C, 60.65; H, 7.05; N, 15.30

IR (CHCl$_3$): 3295, 2975, 1710, 1675 cm$^{-1}$

NMR (CDCl$_3$): 2.00 (quint, J=7 Hz, 2H), 2.57 (t, J=7 Hz, 2H), 3.27 (t, J=6 Hz, 2H), 3.53 (q, J=6 Hz, 2H), 3.73 (s, 3H), 3.84 (t, J=7 Hz, 2H), 6.59, 6.77 (A$_2$B$_2$, J=9 Hz, 4H), 8.62 (br., 1H)

EXAMPLES 2–29

The reactions were carried out in the same method as in Example 1 mentioned above, whereby the compounds (Ia) were obtained. The reaction conditions and their properties are shown in Tables 1 and 2, respectively.

TABLE 1

| | III-1 | Compound (V) | | $K_2CO_3$ | NaI | Reaction Conditions | | | Ia | | |
|---|---|---|---|---|---|---|---|---|---|---|---|
| Ex. No. | g (mmol) | $Z^1$ | $Z^2$ | g (mmol) | g (mmol) | g (mmol) | DMF (ml) | Time | Temp. (°C.) | Yield (g) | Yield (%) | Compd. No. |
| 2 | 2.0 (10.5) | —⟨◯⟩—OMe | Me | 1.73 (12.6) | 3.63 (26.2) | 2.36 (15.8) | 25 | 5 d. | 100–105 | 2.00 | 65.4 | Ia-2 |

TABLE 1-continued $$\text{(III-1)} \quad \underset{O}{\underset{\|}{N}}-CONH(CH_2)_2Cl \quad \xrightarrow{HN\begin{subarray}{l}Z^1\\Z^2\end{subarray}\ (V)} \quad \underset{O}{\underset{\|}{N}}-CONH(CH_2)_2-N\begin{subarray}{l}Z^1\\Z^2\end{subarray} \quad \text{(Ia)}$$

| Ex. No. | III-1 g (mmol) | Compound (V) Z¹ | Z² | g (mmol) | K₂CO₃ g (mmol) | NaI g (mmol) | DMF (ml) | Reaction Conditions Time | Temp. (°C.) | Ia Yield (g) | Yield (%) | Compd. No. |
|---|---|---|---|---|---|---|---|---|---|---|---|---|
| 3 | 2.86 (15.0) | 4-MeO-C₆H₄- | Et | 2.50 (16.5) | 5.18 (37.5) | 3.37 (22.5) | 30 | 6 d. | 100–105 | 2.10 | 45.8 | Ia-3 |
| 4 | 3.15 (16.5) | 4-MeO-C₆H₄- | n-Pr | 3.00 (18.2) | 5.70 (41.3) | 3.71 (24.8) | 35 | 7 d. | 100–105 | 2.23 | 42.2 | Ia-4 |
| 5 | 2.0 (10.5) | 2,4-(MeO)₂-C₆H₃- | H | 1.60 (10.5) | 2.16 (15.7) | 1.0 (6.67) | 30 | 8 d. | 95–100 | 0.64 | 20.0 | Ia-5 |
| 6 | 3.0 (15.7) | 3,4,5-(MeO)₃-C₆H₂- | H | 2.88 (15.7) | 3.24 (23.6) | 3.54 (23.6) | 35 | 5 d. | 95–100 | 2.59 | 49.0 | Ia-6 |
| 7 | 3.0 (15.7) | C₆H₅-CH₂- | H | 2.52 (23.5) | 3.22 (23.5) | 3.52 (23.5) | 35 | 4 d. | 85 | 1.15 | 28.0 | Ia-7 |
| 8 | 1.6 (8.39) | C₆H₅-CH₂- | Me | 1.037 (8.56) | 1.96 (14.3) | 0.3 (2.0) | 20 | 4.6 d. | 80–90 | 1.26 | 54.5 | Ia-8 |
| 9 | 2.86 (15.0) | C₆H₅-CH₂- | C₆H₅- | 3.02 (16.5) | 5.18 (37.5) | 3.37 (22.5) | 30 | 12 d. | 100–105 | 0.60 | 11.9 | Ia-9 |
| 10 | 1.50 (7.87) | 4-MeO-C₆H₄-CH₂- | H | 1.08 (7.87) | 1.63 (11.8) | 1.60 (10.7) | 20 | 2.9 d. 20 hr. | 55–60 95–100 | 0.89 | 20.2 | Ia-10 |
| 11 | 3.60 (18.9) | 4-Me-C₆H₄-CH₂- | H | 2.40 (19.8) | 6.53 (47.3) | 4.25 (28.4) | 35 | 4.5 d. | 85–90 | 1.62 | 31.1 | Ia-11 |
| 12 | 1.50 (7.87) | 4-Cl-C₆H₄-CH₂- | H | 1.11 (7.87) | 1.63 (11.8) | 1.6 (10.7) | 20 | 2.8 d. 17 hr. | 55–60 100 | 1.36 | 25.2 | Ia-12 |

TABLE 1-continued

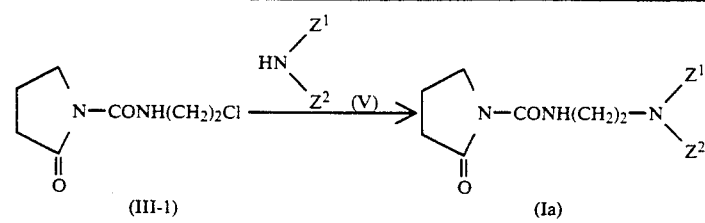

| Ex. No. | III-1 g (mmol) | Compound (V) Z¹ | Z² | $K_2CO_3$ g (mmol) | NaI g (mmol) | Reaction Conditions DMF (ml) | Time | Temp. (°C.) | Ia Yield (g) | Yield (%) | Compd. No. |
|---|---|---|---|---|---|---|---|---|---|---|---|
| 13 | 2.0 (10.5) | MeO–CH₂–C₆H₃–OMe | H | 2.14 (10.5) | 5.10 (36.8) | 0.79 (5.25) | 30 | 7.5 d. | 80–90 | 0.98 | 14.5 | Ia-13 |
| 14 | 3.0 (15.7) | piperidinyl-NCH₂-phenyl | | 2.90 (16.5) | 3.24 (23.6) | 3.54 (23.6) | 30 | 2.2 d. | 90–95 | 2.87 | 55.2 | Ia-14 |
| 15 | 3.0 (15.7) | piperidinyl-N-phenyl | | 2.67 (16.5) | 3.24 (23.6) | 3.54 (23.6) | 30 | 3.2 d. | 95–100 | 3.50 | 70.3 | Ia-15 |
| 16 | 3.0 (15.7) | piperidinyl-N-(2-MeO-phenyl) | | 3.54 (23.6) | 3.24 (23.6) | 3.54 (23.6) | 30 | 3.8 d. | 90–95 | 4.58 | 84.0 | Ia-16 |
| 17 | 1.91 (10.02) | piperidinyl-N-(4-OMe-phenyl) | | 2.30 (10.06) | 2.25 (15.0) | 2.86 (15.0) | 20 | 2.9 d. | 90–95 | 1.68 | 48.4 | Ia-17 |
| 18 | 1.91 (10.02) | piperidinyl-N-(2-pyrimidinyl) | | 2.37 (10.0) | 4.1 (30.0) | 2.25 (15.0) | 30 | 5 d. | 90–95 | 1.18 | 37.0 | Ia-18 |
| 19 | 5.0 (26.2) | piperidinyl-N-CH₂CH₂OH | | 3.76 (28.9) | 7.24 (52.4) | 5.89 (39.3) | 50 | 5 d. | 90 | 4.38 | 58.8 | Ia-19 |
| 20 | 1.50 (7.89) | piperidinyl-NSO₂-(4-Cl-phenyl) | | 2.16 (8.28) | 2.18 (1.58) | 1.77 (1.18) | 20 | 4 d. | 100–105 | 1.66 | 50.8 | Ia-20 |
| 21 | 1.64 (8.60) | piperidinyl-NSO₂-(4-F-phenyl) | | 2.21 (9.03) | 2.38 (17.2) | 1.93 (12.9) | 25 | 3.8 d. | 100–105 | 1.10 | 32.1 | Ia-21 |
| 22 | 1.64 (8.60) | piperidinyl-NSO₂-(4-OMe-phenyl) | | 2.36 (9.21) | 2.38 (17.2) | 1.93 (12.9) | 25 | 4 d. | 100–105 | 0.65 | 50.8 | Ia-22 |

TABLE 1-continued $$\underset{(III-1)}{\text{pyrrolidinone-N-CONH(CH}_2)_2\text{Cl}} \xrightarrow{\underset{Z^2}{\overset{Z^1}{\text{HN}}} \quad (V)} \underset{(Ia)}{\text{pyrrolidinone-N-CONH(CH}_2)_2-\text{N}\underset{Z^2}{\overset{Z^1}{<}}}$$

| Ex. No. | III-1 g (mmol) | Compound (V) Z¹ | Z² | g (mmol) | K₂CO₃ g (mmol) | NaI g (mmol) | Reaction Conditions DMF (ml) | Time | Temp. (°C.) | Ia Yield (g) | Yield (%) | Compd. No. |
|---|---|---|---|---|---|---|---|---|---|---|---|---|
| 23 | 2.42 (12.7) | piperidyl | NSO₂N(Me)₂ | 2.80 (14.5) | 3.51 (25.4) | 2.86 (19.1) | 30 | 5 d. | 100 | 2.02 | 45.8 | Ia-23 |
| 24 | 2.30 (12.1) | cyclohexyl-C(=O)NH | N-phenyl-ethyl | 2.93 (12.7) | 3.32 (24.2) | 2.72 (18.2) | 25 | 3.2 d. | 100 | 3.29 | 65.5 | Ia-24 |
| 25 | 0.89 (4.67) | OH, (4-Cl-phenyl), dipropyl | | 0.99 (4.68) | 0.97 (7.02) | 1.05 (7.01) | 10 | 2.9 d. | 90–95 | 1.48 | 86.6 | Ia-25 |
| 26 | 3.00 (15.7) | piperazinyl-(2-pyridyl) | | 2.82 (17.3) | 5.38 (39.2) | 3.53 (23.5) | 55 | 5 d. | 115 | 3.1 | 62.0 | Ia-26 |
| 27 | 2.56 (13.4) | OH, phenyl, dipropyl | | 2.50 (14.1) | 4.63 (33.5) | 3.0 (20.1) | 30 | 3 d. | 100–105 | 3.07 | 69.0 | Ia-27 |
| 28 | 1.15 (6.03) | OH, (4-OCH₃-phenyl), dipropyl | | 1.25 (6.03) | 2.08 (15.1) | 1.36 (9.04) | 20 | 3 d. | 100–105 | 1.65 | 75.7 | Ia-28 |
| 29 | 0.96 (5.06) | cyclohexyl, (4-Cl-phenyl) | | 1.0 (5.16) | 1.75 (12.6) | 1.14 (7.59) | 20 | 3.75 d. | 100–105 | 0.34 | 19.4 | Ia-29 |
| 30 | 2.81 (14.7) | OH, (2-thienyl), cyclohexyl | | 2.70 (14.7) | 6.10 (44.1) | 3.30 (22.0) | 30 | 4 d. | 100–105 | 3.89 | 78.2 | Ia-30 |

TABLE 1-continued $$\underset{(III-1)}{\text{pyrrolidinone-N-CONH(CH}_2)_2\text{Cl}} \xrightarrow{\underset{Z^2}{\overset{Z^1}{HN}} \quad (V)} \underset{(Ia)}{\text{pyrrolidinone-N-CONH(CH}_2)_2-N\overset{Z^1}{\underset{Z^2}{}}}$$

| Ex. No. | III-1 g (mmol) | Compound (V) Z¹ | Compound (V) Z² | Compound (V) g (mmol) | $K_2CO_3$ g (mmol) | NaI g (mmol) | DMF (ml) | Reaction Conditions Time | Temp. (°C.) | Ia Yield (g) | Ia Yield (%) | Compd. No. |
|---|---|---|---|---|---|---|---|---|---|---|---|---|
| 31 | 2.08 (10.9) | (cyclohexyl-OH) | (thienyl-S) | 2.00 (10.9) | 4.52 (32.7) | 2.45 (16.4) | 30 | 4 d. | 100–105 | 1.91 | 51.9 | Ia-31 |
| 32 | 2.79 (14.6) | (cyclohexyl-OH) | (4-Cl-phenyl) | 3.10 (14.6) | 6.05 (43.8) | 3.28 (21.9) | 35 | 5 d. | 100–105 | 4.25 | 79.4 | Ia-32 |
| 33 | 1.80 (9.46) | (cyclohexenyl) | (thienyl-S) | 1.72 (8.53) (.HCl salt) | 3.92 (2.84) | 2.13 (1.42) | 30 | 4 d. | 100–105 | 2.38 | 87.4 | Ia-33 |

TABLE 2

| Compound No. | m.p. (°C.) (Recrystallizing solvent) | Elementary Analysis Found (Calcd.) (%) | IR (cm$^{-1}$) (CHCl$_3$) | NMR (CDCl$_3$) δ |
|---|---|---|---|---|
| Ia-2 | 84.5–85.5 (Et$_2$O) | C$_{15}$H$_{21}$N$_3$O$_3$<br>C, 61.73 (61.84)<br>H, 7.26 (7.27)<br>N, 14.39 (14.42) | 3300, 1705, 1680<br>1540, 1510 | 1.75–2.15(m, 2H), 2.55(t, J=7Hz, 2H), 2.90(s, 3H), 3.40(s, 4H), 3.74(s, 3H), 3.80(t, J=7Hz, 2H), 6.80(s, 4H), 8.50(br., 1H) |
| Ia-3 | 87.0–88.5 (Et$_2$O) | C$_{15}$H$_{23}$N$_3$O$_3$<br>C, 62.93 (62.93)<br>H, 7.64 (7.59)<br>N, 13.73 (13.76) | 3300, 1705, 1670<br>1530 (sh), 1505 | 1.10(t, J=7Hz, 3H), 1.80–2.16(m, 2H), 2.57(t, J=7Hz, 2H), 3.28(q, J=7Hz, 2H), 3.36(s, 3H), 3.83(t, J=7Hz, 2H), 6.80(s, 4H), 8.54(br., 1H) |
| Ia-4 | 70.0–71.0 (Et$_2$O) | C$_{17}$H$_{25}$N$_3$O$_3$<br>C, 64.09 (63.92)<br>H, 7.90 (7.89)<br>N, 13.18 (13.16) | 3280, 1700, 1670<br>1530 (sh), 1500 | 0.90(t, J=7Hz, 3H), 1.55(quint, J=7Hz, 2H), 2.00(quint, J=7Hz, 2H), 2.56(t, J=7Hz, 2H), 3.16(t, J=7Hz, 2H), 3.33 (s, 4H), 3.73(s, 3H), 3.83(t, J=7Hz, 2H), 6.80(s, 4H), 8.54(br., 1H) |
| Ia-5 | — | C$_{15}$H$_{21}$N$_3$O$_4$<br>C, 58.53 (58.62)<br>H, 6.84 (6.89)<br>N, 13.46 (13.67) | 3300, 1710, 1680<br>1615, 1600<br>1540 (sh), 1520 | 2.00(quint, J=7Hz, 2H), 2.57(t, J=7Hz, 2H), 3.20–3.60(m, 4H), 3.73(s, 3H), 3.78(s, 3H), 3.85(t, J=7Hz, 2H), 4.50 (br., 1H), 6.13(dd, J$_1$=9Hz, J$_2$=2Hz, 1H) 6.23(d, J=2Hz, 1H), 6.64(d, J=9Hz, 1H), 8.60(br., 1H) |
| Ia-6 | 124.0–125.5 (EtOH) | C$_{16}$H$_{23}$N$_3$O$_5$<br>C, 59.56 (56.96)<br>H, 6.85 (6.87)<br>N, 12.32 (12.46) | 3290, 1700, 1665<br>1600, 1535, 1500 | 2.00(quint, J=7Hz, 2H), 2.57(t, J=7Hz, 2H), 3.29(q, J=6Hz, 2H), 3.51(q, J=6Hz, 2H), 3.71(s, 3H), 3.80(s, 6H), 3.84(t, J=7Hz, 2H), 5.85(s, 2H), 8.60(br., 1H) |
| Ia-7 | maleate<br>143.0–144.0<br>(i-PrOH) | C$_{14}$H$_{19}$N$_3$O$_2$·C$_4$H$_4$O$_4$<br>C, 57.17 (57.28)<br>H, 6.32 (6.14)<br>N, 11.12 (11.14) | (free base)<br>3290, 1700, 1670<br>1535 | (free base)<br>1.80–2.13(m, 2H), 2.56(t, J=7H, 2H), 2.79 (t, J=6Hz, 2H), 3.40(q, J=6Hz, 2H), 3.80 (s, 2H), 3.80(t, J=7Hz, 2H), 7.30(s, 5H), 8.60(br., 1H) |
| Ia-8 | maleate<br>130.0–130.5<br>(i-PrOH) | C$_{15}$H$_{21}$N$_3$O$_2$·C$_4$H$_4$O$_4$<br>C, 58.24 (58.30)<br>H, 6.46 (6.44)<br>N, 10.70 (10.74) | (free base)<br>3300, 1705, 1675<br>1530 | (free base)<br>2.00(quint, J=7Hz, 2H), 2.48–2.70(m, 4H), 2.87(s, 3H), 3.43(q, J=6Hz, 2H), 3.54(s, 2H), 3.83(t, J=7Hz, 2H), 7.20–7.40(m, 5H), 8.67(br., 1H) |
| Ia-9 | 97.0–98.0 (Et$_2$O) | C$_{20}$H$_{23}$N$_3$O$_2$<br>C, 71.19 (71.19)<br>H, 6.91 (6.87)<br>N, 12.46 (12.45) | 3290, 1705, 1675<br>1590, 1530, 1500 | 1.98(quint, J=7Hz, 2H), 2.56(t, J=7Hz, 2H) 3.58(s, 4H), 3.81(t, J=7Hz, 2H), 4.59(s, 2H), 6.60–7.30(m, 10H), 8.53(br., 1H) |
| Ia-10 | maleate | C$_{15}$H$_{21}$N$_3$O$_3$·C$_4$H$_4$O$_4$ | (free base) | (free base) |

TABLE 2-continued

| Compound No. | m.p. (°C.) (Recrystallizing solvent) | Elementary Analysis Found (Calcd.) (%) | IR (cm⁻¹) (CHCl₃) | NMR (CDCl₃) δ |
|---|---|---|---|---|
| | 142.5-143.5 (i-PrOH) | C, 55.98 (56.01) H, 6.25 (6.19) N, 10.27 (10.31) | 3300, 1710, 1680 1610, 1580, 1540 1505 | 1.80-2.15(m, 2H), 2.57(t, J=7Hz, 2H), 2.77 (t, J=6Hz, 2H), 3.40(q, J=6Hz, 2H), 3.76 (s, 3H), 3.80(t, J=7Hz, 2H), 6.85, 7.23 (A₂B₂, J=9Hz, 4H), 8.60(br., 1H) |
| Ia-11 | maleate 155.0-156.0 (i-PrOH) | C₁₅H₂₁N₃O₂·C₄H₄O₄ C, 58.11 (58.30) H, 6.43 (6.44) N, 10.68 (10.74) | (free base) 3290, 1700, 1670 1535 | (free base) 1.98(quint, J=7Hz, 2H), 2.30(s, 3H), 2.55 (t, J=7Hz, 2H), 2.77(t, J=6Hz, 2H), 3.39 (q, J=6Hz, 2H), 3.75(s, 2H), 3.80(t, J=7Hz 2H), 7.10, 7.20(A₂B₂, J=9Hz, 4H), 8.58 (br., 1H) |
| Ia-12 | maleate 161.5-162.0 (i-PrOH) | C₁₄H₁₈N₃O₂Cl·C₄H₄O₄ C, 52.47 (52.50) H, 5.31 (5.38) N, 10.26 (10.20) Cl, 8.69 (8.61) | (free base) 3300, 1705, 1675 1540 | (free base) 1.99(quint, J=7Hz, 2H), 2.57(t, J=7Hz, 2H) 2.75(t, J=6Hz, 2H), 3.39(q, J=6Hz, 2H), 3.75(s, 2H), 3.80(t, J=7Hz, 2H), 7.28(s, 4H), 8.60(br., 1H) |
| Ia-13 | — | C₁₆H₂₃N₃O₄·1/5CH₂Cl₂ C, 57.59 (57.51) H, 7.06 (6.97) N, 12.66 (12.42) | 3300, 1705, 1670 1610, 1580, 1545 1500 | 1.97(quint, J=7Hz, 2H), 2.54(t, J=7Hz, 2H) 2.80(t, J=6Hz, 2H), 3.47(q, J=6Hz, 2H), 3.74 (s, 2H), 3.78(t, J=7Hz, 2H), 3.80(s, 6H), 6.43(br., 2H), 7.20(d, J=9Hz, 1H), 8.60(br., 1H) |
| Ia-14 | 80.5-81.5 (Et₂O—n-Hexane = 2:1 v/v) | C₁₈H₂₆N₄O₂ C, 65.52 (65.43) H, 7.97 (7.93) N, 16.94 (16.96) | 3300, 1705, 1670 1540, 1520 (sh) | 2.00(quint, J=7Hz, 2H), 2.45-2.70(m, 12H), 3.40(q, J=6Hz, 2H), 3.50(s, 2H), 3.84(t, J=7Hz, 2H), 7.30(s, 5H), 8.63(br., 1H) |
| Ia-15 | 133.0-134.0 (Et₂O—n-Hexane = 1:1 v/v) | C₁₇H₂₄N₄O₂ C, 64.52 (64.53) H, 7.60 (7.65) N, 17.62 (17.71) | 3280, 1700, 1670 1590, 1520, 1485 | 2.00(quint, J=7Hz, 2H), 2.50-2.70(m, 8H), 3.13-3.27(m, 4H), 3.45(q, J=6Hz, 2H), 3.84 (t, J=7Hz, 2H), 6.73-7.00(m, 3H), 7.13-7.30 (m, 2H), 8.65(br., 1H) |
| Ia-16 | maleate 180.0-183.0 (d) (i-PrOH—MeOH) | C₁₈H₂₆N₄O₃·C₄H₄O₄ C, 57.03 (57.13) H, 6.72 (6.54) N, 12.14 (12.12) | (free base) 3300, 1700, 1665 1580, 1520, 1490 | (free base) 1.97(quint, J=7Hz, 2H), 2.45-2.70(m, 6H), 3.04-3.20(m, 4H), 3.45(q, J=6Hz, 2H), 3.82 (t, J=7Hz, 2H), 3.84(s, 3H), 6.92(s, 4H), 8.65(br., 1H) |
| Ia-17 | 124.5-125.5 (Et₂O—CH₂Cl₂) | C₁₈H₂₆N₄O₃ C, 62.43 (62.41) H, 7.48 (7.56) N, 16.31 (16.17) | 3300, 1705, 1670 1540 (sh), 1505 | 2.00(quint, J=7Hz, 2H), 2.50-2.70(m, 8H), 3.05-3.17(m, 4H), 3.47(q, J=6Hz, 2H), 3.75 (s, 3H), 3.85(t, J=7Hz, 2H), 6.87(A₂B₂, J= 9Hz, 4H), 8.67(br., 1H) |
| Ia-18 | 80.5-81.5 (Et₂O) | C₁₅H₂₂N₆O₂ C, 56.62 (56.69) H, 6.94 (6.96) N, 26.28 (26.40) | 3300, 1705, 1670 1580, 1540, 1500 1485 (sh) | 2.01(quint, J=7Hz, 2H), 2.47-2.70(m, 8H), 3.45(q, J=6Hz, 2H), 3.75-3.93(m, 6H), 6.45 (t, J=5Hz, 1H), 8.27(d, J=5Hz, 2H), 8.68 (br., 1H) |
| Ia-19 | 109.0-111.0 (Et₂O) | C₁₃H₂₄N₄O₃ C, 54.68 (54.91) H, 8.40 (8.51) N, 19.56 (19.71) | 3300, 1705, 1675 1520 | 2.02(quint, J=7Hz, 2H), 2.47-2.70(m, 14H), 3.04(s, 1H), 3.40(q, 6Hz, 2H), 3.62(t, J= 6Hz, 2H), 3.87(t, J=7Hz, 2H), 8.64(br., 1H) |
| Ia-20 | 149.0-150.0 (EtOH) | C₁₇H₂₃N₄O₄SCl C, 49.09 (49.21) H, 5.49 (5.59) N, 13.35 (13.50) S, 7.71 (7.73) Cl, 8.40 (8.54) | 3290, 1700, 1670 1580, 1530 | 2.00(quint, J=7Hz, 2H), 2.45-2.65(m, 8H), 3.00-3.13(m, 4H), 3.37(q, J=6Hz, 2H), 3.82 (t, J=7Hz, 2H), 7.53-7.74(A₂B₂, J=9Hz, 4H) 8.52(br., 1H) |
| Ia-21 | 110.5-111.5 (EtOH) | C₁₇H₂₃N₄O₄SF C, 51.05 (51.24) H, 5.59 (5.82) N, 13.87 (14.06) S, 8.26 (8.05) F, 5.03 (4.77) | 3300, 1705, 1675 1590, 1525, 1490 | 1.85-2.16(m, 2H), 2.46-2.60(m, 8H), 3.00-3.12(m, 4H), 3.36(q, J=6Hz, 2H), 3.81 (t, J=7Hz, 2H), 7.22(t, J=9Hz, 2H), 7.78 (d-d, J₁=9Hz, J₂=6Hz, 2H), 8.52(br., 1H) |
| Ia-22 | 186.5-187.5 (EtOH) | C₁₈H₂₆N₄O₅S C, 52.54 (52.67) H, 6.39 (6.38) N, 13.53 (13.65) S, 7.84 (7.81) | 3310, 1705, 1675 1595, 1575, 1530 1490 | 1.80-2.15(m, 2H), 2.40-2.65(m, 8H), 2.96-3.08(m, 4H), 3.35(q, J=6Hz, 2H), 3.80(t, J=7Hz, 2H), 8.85(s, 3H), 7.00, 7.65 (A₂B₂, J=9Hz, 4H), 8.47(br., 1H) |
| Ia-23 | 97.0-97.5 (EtOH) | C₁₃H₂₅N₅O₄S C, 44.87 (44.97) H, 7.15 (7.25) N, 20.13 (20.16) S, 9.13 (9.23) | 3290, 1700, 1670 1520 | 1.83-2.17(m, 2H), 2.40-2.67(m, 8H), 2.80 (s, 6H), 3.20-3.50(m, 6H), 3.83(t, J=7Hz, 2H), 8.62(br., 1H) |
| Ia-24 | 195.0-200.0 (EtOH) | C₂₀H₂₇N₅O₃·C₂H₅OH C, 61.18 (61.23) H, 7.49 (7.71) N, 16.84 (16.23) | 3425, 3270, 1710 1675, 1600, 1515 1495 | 1.64-2.20(m, 4H), 2.53-2.85(m, 10H), 3.44 (q, J=6Hz, 2H), 3.86(t, J=7Hz, 2H), 4.73 (s, 2H), 6.70-7.40(m, 5H), 7.64(br. s, 1H), 8.88(br., 1H) |
| Ia-25 | 152.5-153.5 (Et₂O—CH₂Cl₂) | C₁₈H₂₄N₃O₃Cl C, 58.87 (59.09) H, 6.54 (6.61) N, 11.28 (11.49) Cl, 9.52 (9.69) | 3580, 3300, 1705 1670, 1525 | 1.62-2.30(m, 6H), 2.40-2.85(m, 8H), 3.42 (q, J=6Hz, 2H), 3.80(t, J=7Hz, 2H), 7.29, 7.43(A₂B₂, J=9Hz, 4H), 8.65(br., 1H) |
| Ia-26 | dimaleate 149.0-150.0 (MeOH—i-PrOH) | C₁₆H₂₃N₅O₂·2C₄H₄O₄ C, 52.2 (52.45) H, 5.75 (5.69) | (Nujol) dimaleate 3310, 1715, 1680 | (free base) 1.85-2.17(m, 2H), 2.50-2.63(m, 6H), 3.35-3.60(m, 6H), 3.84(t, J=7Hz, 2H), 6.50-6.73 |

TABLE 2-continued

| Compound No. | m.p. (°C.) (Recrystallizing solvent) | Elementary Analysis Found (Calcd.) (%) | IR (cm$^{-1}$) (CHCl$_3$) | NMR (CDCl$_3$) δ |
|---|---|---|---|---|
| | | N, 12.69 (12.75) | 1630, 1610 | (m, 2H), 7.28–7.55(m, 1H), 8.17(d-d, J$_1$=9Hz, J$_2$=2Hz, 1H), 8.69(br., 1H) |
| Ia-27 | 113.0–114.0 (EtOH) | C$_{18}$H$_{25}$N$_3$O$_3$ C, 65.29 (65.23) H, 7.61 (7.60) N, 12.67 (12.68) | 3260, 2910, 1705 1670, 1520 | 1.70–2.90(m, 16H), 3.45(q, J=6Hz, 2H), 3.85(t, J=7Hz, 2H), 7.36, 5.51(A$_2$B$_2$, J=9Hz, 4H), 8.66(br., 1H) |
| Ia-28 | 105.5–106.5 (i-PrOH—Et$_2$O) | C$_{19}$H$_{27}$N$_3$O$_4$ C, 63.02 (63.14) H, 7.58 (7.53) N, 11.47 (11.63) | 3290, 2930, 1705 1675, 1610, 1505 | 1.68–2.85(m, 15H), 3.43(q, J=6Hz, 2H), 3.79(s, 3H), 3.82(t, J=7Hz, 2H), 6.86, 7.43(A$_2$B$_2$, J=9Hz, 4H), 8.64(br., 1H) |
| Ia-29 | 141.5–142.5 (i-PrOH) | C$_{18}$H$_{22}$N$_3$O$_2$Cl C, 62.24 (62.15) H, 6.36 (6.37) N, 12.05 (12.08) Cl, 10.23 (10.19) | 3290, 2895, 1700 1670, 1530 | 2.03(quint, J=7Hz, 2H), 2.50–2.80(m, 8H), 3.21(q, J=3Hz, 2H), 3.51(q, J=6Hz, 2H), 3.87(q, J=7Hz, 2H), 6.06(br., 1H), 7.20–7.37(m, 4H), 8.60(br., 1H) |
| Ia-30 | 126.0–126.5 (CH$_2$Cl$_2$—Et$_2$O) | C$_{16}$H$_{23}$N$_3$O$_3$S C, 56.89 (56.95) H, 6.84 (6.87) N, 12.41 (12.45) S, 9.41 (9.50) | 3560, 3350, 1705 1670, 1530 | 1.90–2.30(m, 7H), 2.50–2.80(m, 8H), 3.443(q, J=5.4Hz, 2H), 3.857(t, J=7.2Hz, 2H), 6.90–7.30(m, 3H), 8.650(br., 1H) |
| Ia-31 | tartrate powder | C$_{16}$H$_{23}$N$_3$O$_3$S·C$_4$H$_6$O$_6$·½H$_2$O C, 48.62 (48.38) H, 6.18 (6.09) N, 8.12 (8.46) S, 6.33 (6.46) | (Nujol) L-tartrate 3380, 3280, 1700 1670, 1600, 1535 | (free base) 1.65–1.90(m, 2H), 1.95–2.15(m, 5H), 2.417, 2.881(ABq, J=11Hz, 2H), 2.55–2.65 (m, 4H), 2.934(d, J=10Hz, 1H), 3.30–3.50 (m, 2H), 3.855(t, J=7Hz, 2H), 4.219 (s, 1H), 6.954–6.973(m, 2H), 7.182–7.222 (m, 1H), 8.918(br. s, 1H) |
| Ia-32 | 119.5–120.5 (Et$_2$O-toluene) | C$_{18}$H$_{24}$N$_3$O$_3$Cl C, 59.11 (59.09) H, 6.45 (6.61) N, 11.49 (11.49) Cl, 9.96 (9.96) | 3500, 3280, 1705 1675, 1545, 1525 1485 | 1.65–2.15(m, 7H), 2.404(a part of ABq, J=11Hz, 1H), 2.55–2.75(m, 5H), 2.975(d, J=10Hz, 1H), 3.418(m, 2H), 3.867(t, J=7Hz, 2H), 4.162(s, 1H), 7.272–7.501(m, 3H), 8.929(br., 1H) |
| Ia-33 | tartrate powder | C$_{16}$H$_{21}$N$_3$O$_2$S·C$_4$H$_6$O$_6$·½H$_2$O C, 49.78 (50.20) H, 5.82 (5.90) N, 8.33 (8.78) S, 6.37 (6.70) | (Nujol) L-tartrate 3260, 1700, 1670 (sh), 1650(sh), 1590, 1525 | (free base) 2.020(quint, J=7Hz, 2H), 2.355(s, 2H) 2.590(t, J=7Hz, 2H), 2.63–2.75(m, 6H), 3.37–3.40(m, 2H), 3.518(q, J=6Hz, 2H), 3.858(t, J=7Hz, 2H), 6.16–6.20(m, 1H), 6.88–7.19(m, 3H) |

EXAMPLE 34

2-Oxo-1-[[2-(1,2,4-triazol-1-yl)ethyl]carbamoyl]pyrrolidine (Ia-34)

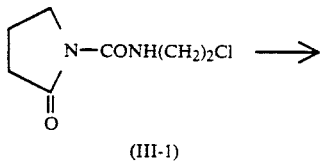

(III-1)

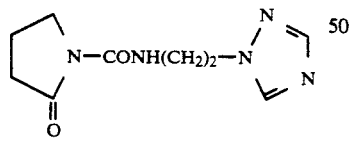

(Ia-34)

To a solution of 1.9 g (27.5 mmol) of 1,2,4-triazole in 15 ml of DMF was added 1.1 g (27.5 mmol) of 60% NaH, and the mixture was heated at 90° C. for about 2 hr. Then, 13 ml of DMF containing 3.50 g (18.4 mmol) of 1-[(2-chloroethyl)carbamoyl]-2-oxopyrrolidine (III-1) was added to the mixture, which was heated at 90° C. for 4.5 hr. The reaction solution was poured into CH$_2$Cl$_2$, and the insoluble material was removed by filtration. After evaporating the solvent, the CH$_2$Cl$_2$ layer was refined by silica gel column chromatography, whereby 2.28 g (55.6%) of the objective compound (Ia-34) was obtained from the eluate with CH$_2$Cl$_2$-methanol (20/1 v/v). The crystals melting at 106.0°–107.0° C. were obtained by recrystallizing from ethanol.

Anal. Calcd. (%) for C$_9$H$_{13}$N$_5$O$_2$: C, 48.42; H, 5.87; N, 31.38

Found (%): C, 48.47; H, 5.77; N, 31.19

IR (CHCl$_3$): 3300, 1710, 1685, 1530, 1505 (sh), 1485, 1455, 1430 cm$^{-1}$

NMR (CDCl$_3$): 1.85–2.20 (m, 2H), 2.58 (t, J=7 Hz, 2H), 3.65–3.90 (m, 4H), 4.37 (t, J=7 Hz, 2H), 7.97 (s, 1H), 8.08 (s, 1H), 8.55 (br., 1H)

EXAMPLE 35

2-Oxo-1-[[2-(1H-imidazol-1-yl)ethyl]carbamoyl]pyrrolidine (Ia-35)

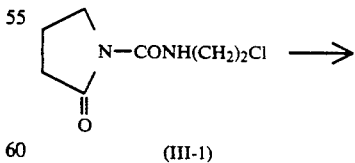

(III-1)

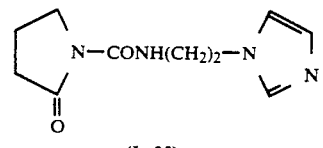

(Ia-35)

In the same method as in Example 34 described above, 3.0 g (15.7 mmol) of 1-[(2-chloroethyl)carbamoyl]-2-oxopyrrolidine (III-1) was reacted with a solution of 1.29 g (18.9 mmol) of 1H-imidazole in 24 ml of DMF at 110° C. for 6.5 hr. in the presence of 0.75 g (18.9 mmol) of 60% NaH, whereby the compound (Ia-35) was obtained.

Yield: 1.22 g; 34.9%
m.p.: 130.5°–131.5° C. (Et₂O)
Anal. Calcd. (%) for C₁₀H₁₄N₄O₂: C, 54.04; H, 6.35; N, 25.21
Found (%): C, 53.89; H, 6.29; N, 25.00
IR (CHCl₃): 3300, 1710, 1680 (sh), 1540, 1510 (sh) cm⁻¹
NMR (CDCl₃): 1.86–2.20 (m, 2H), 2.60 (t, J=7 Hz, 2H), 3.60 (q, J=6 Hz, 2H), 3.83 (t, J=7 Hz, 2H), 4.12 (t, J=6 Hz, 2H), 6.95 (s, 1H), 7.07 (s, 1H), 7.48 (s, 1H), 8.55 (br., 1H)

EXAMPLE 36

1-[[2-(4-Methoxyphenyl)aminoethyl]carbamoyl]-2-oxopyrrolidine (Ia-1)

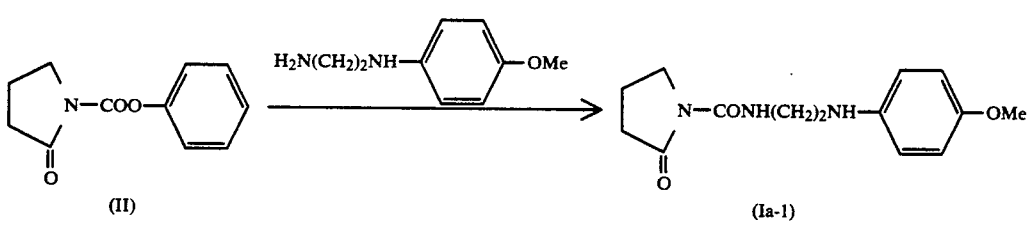

A mixture of 4.0 g (19.5 mmol) of 1-phenoxycarbonyl-2-oxopyrrolidine and 3.4 g (20.4 mmol) of 2-(4-methoxyphenylamino)ethylamine was heated at 115°–120° C. for 4 hr. The reaction solution was refined by silica gel column chromatography, whereby 4.94 g (87.0%) of the objective product (Ia-1) was obtained from the eluate with toluene-ethyl acetate (3/1 v/v). The needles melting at 83.5°–84.5° C. were obtained by recrystallizing from ethanol.

EXAMPLES 37–38

The reactions were carried out in the same method as in Example 36 described above. The reaction conditions and their properties of each objective compounds are shown in Tables 3 and 5, respectively.

TABLE 3

| | | | | Reaction Conditions | Compound (Ia) Yield | | |
|---|---|---|---|---|---|---|---|
| Ex. No. | Compound (II) g (mmol) | Compound (IV) R | g (mmol) | Temp. (°C.) Time | (g) | (%) | Compound No. |
| 37 | 2.86 (13.9) | —NH—⌬—Me | 2.2 (14.6) | 115–120 5.5 hr. | 3.21 | 88.1 | Ia-36 |
| 38 | 2.18 (10.6) | —NH—⌬—Cl | 2.0 (11.7) | 120–125 4 hr. | 2.88 | 96.0 | Ia-37 |

EXAMPLE 39

1-[[2-Pyrazol-1-yl)ethyl)carbamoyl]-2-oxopyrrolidine (Ia-38)

To a solution of 3.58 g (14.8 mmol) of 2-phthalimidoethylpyrazole in 45 ml of methanol was added 1.11 g (22.2 mmol) of hydrazine hydrate, and the mixture was refluxed for 7 hr. The solvent was evaporated under reduced pressure, and the residue was washed with CH₂Cl₂ and ethyl acetate, and filtered. The filtrate was evaporated under reduced pressure, and then 2.73 g (13.3 mmol) of 2-oxo-1-phenoxycarbonylpyrrolidine (II) was added to the residue, and the mixture was heated at 115°–120° C. for 3 hr. After cooling, the reaction mixture was refined by silica gel column chromatography, and the resulting crystalline product obtained from the eluate with toluene/ethyl acetate (3/1-1/1 v/v) was recrystallized from ether, whereby 1.91 g (64.7%) of the objective compound (Ia-38) melting at 62.5°–63.5° C. was obtained.

EXAMPLE 40

The reaction was carried out in the same method as mentioned above. The reaction conditions are shown in Table 4 and properties of the objective compounds are shown in Table 5.

TABLE 4

| Ex. No. | Compound (II) g (mmol) | Compound (IV) R | g (mmol) | Reaction Conditions Temp. (°C.) Time | Compound (Ia) Yield (g) (%) | Compound No. |
|---|---|---|---|---|---|---|
| 40 | 4.8 (23.4) | —NH—C(=N—O)—CH₃ | 5.3* (19.5) | 115–120 3 hr. | 3.51   62.8 | Ia-39 |

*phthalimidate

EXAMPLE 41

1-[N-Methyl-[2-(4-methoxyphenyl)aminoethyl]carbamoyl]-2-oxopyrrolidine (Ia-40)

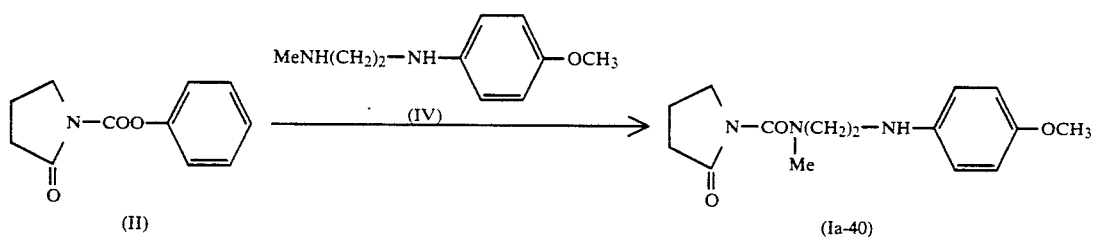

A mixture of 5.31 g (25.9 mmol) of 2-oxo-1-phenoxycarbonylpyrrolidine (II) and 4.67 g (25.9 mmol) of Compound (IV) was heated with stirring at 110°–120° C. for 4 hr. in a bath. After cooling, the reaction solution was refined by silica gel column chromatography, whereby 5.57 g of the oily objective compound (Ia-40) was obtained from the eluate with toluene/ethyl acetate (1/1 v/v) and ethyl acetate, respectively. Yield: 74.0%.

The properties of the objective compound are shown in Table 5.

A mixture of 1.87 g (9.13 mmol) of 2-oxo-1-phenoxycarbonylpyrrolidine (II), 2.39 g (9.13 mmol) of 2-(4-methoxyphenyloxy)ethyl-N-methylamine hydrobromide and 2.30 g (22.8 mmol) of triethylamine in 0.5 ml of DMA was heated at 115°–125° C. for 6.5 hr. and ethyl acetate was added to the reaction solution. The mixture was washed with aqueous NaHCO₃ and water, and dried, then the solvent was distilled off. The residue was refined by silica gel column chromatography, whereby 2.37 g of an oily compound (Ia-41) was obtained from the eluate with toluene/ethyl acetate (5/1-3/1 v/v). Yield: 88.8%.

The properties of the objective compound are shown in Table 5.

EXAMPLE 42

1-[N-Methyl[2-(4-methoxyphenyloxy)ethyl]carbamoyl]-2-oxopyrrolidine (Ia-41)

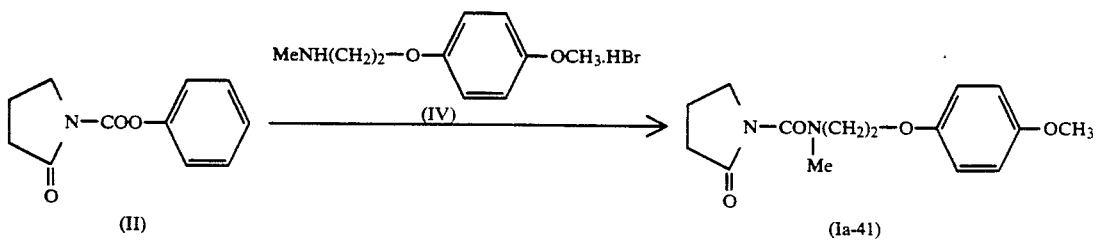

EXAMPLE 43

1-[[2-(4-Methoxyphenyloxy)ethyl]carbamoyl]-2-oxopyrrolidine (Ia-42)

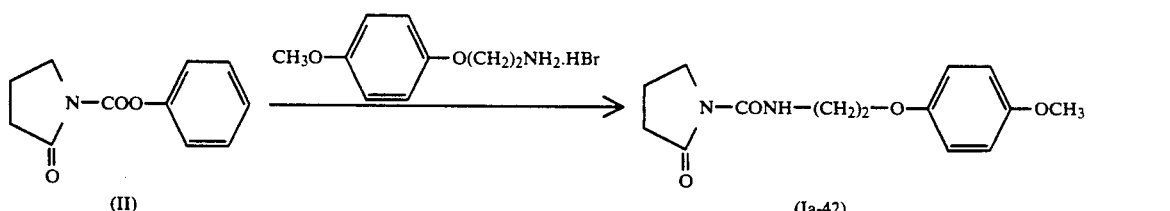

A mixture of 1.16 g (5.64 mmol) of 2-oxo-1-phenoxycarbonylpyrrolidine (II) were added 2.0 g (8.06 mmol) of 2-(4-methoxyphenyloxy)-ethylamine hydrobromide and 1.63 g (16.1 mmol) of triethylamine was heated at 110° C. for 3 hr. After evaporation of the solvent, the residue was refined by silica gel column chromatography, whereby 1.86 g of the objective compound (Ia-42) was obtained as crystals from the eluate with toluene-/ethyl acetate (5/1-3/1 v/v). Yield: 83.0%.

The objective compound melting at 62.5°-64.5° C. was obtained by recrystallizing from ethanol-ether. The properties of the objective compound (Ia-42) are shown in Table 5.

EXAMPLE 44

1-[N-Ethyl-2-(4-methoxyphenyl)(n-propyl)amino]ethyl]carbamoyl]-2-oxopyrrolidine (Ia-43)

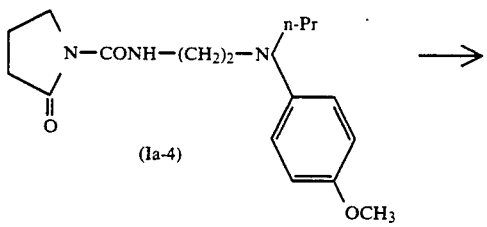

To a mixture of 1.01 g (3.16 mmol) of 1-[2-[(4-methoxyphenyl)-(n-propyl)amino]ethyl]carbamoyl]-2-oxopyrrolidine (Ia-4) in 15 ml of THF was added 126 mg (3.16 mmol) of NaH (60%) at room temperature, and the mixture was stirred for 50 min. Then, the mixture was added to 0.265 ml (3.32 mmol) of EtI and stirred for 3 days at room temperature. The reaction solution was mixed with ethyl acetate and dried, and the solvent was removed by evaporation. The oily residue obtained was refined by silica gel column chromatography, whereby 330 mg of an oily compound (Ia-43) was obtained from the eluate with toluene/ethyl acetate (3/1-1/1 v/v).

Yield: 30%

The properties of the objective compound are shown in Table 5.

TABLE 5

| Compd. No. | m.p. (°C.) (Recrystallizing Solvent) | Elementary Analysis Found (Calcd.) (%) | IR (cm$^{-1}$) (CHCl$_3$) | NMR (CDCl$_3$) δ |
|---|---|---|---|---|
| I a-36 | 102.0–103.0 (EtOH) | $C_{14}H_{19}N_3O_2$<br>C, 64.41 (64.32)<br>H, 7.33 (7.33)<br>N, 16.05 (16.08) | 3280, 1705, 1670<br>1610, 1535, 1510 | 2.00(quint, J=7Hz, 2H), 2.21(s, 3H), 2.57 (t, J=7Hz, 2H), 3.20–3.60(m, 4H), 3.83(t, J=7Hz, 2H), 6.53, 6.96($A_2B_2$, J=9Hz, 4H), 8.57(br., 1H) |
| I a-37 | 141.0–142.0 (EtOH) | $C_{13}H_{16}N_3O_2Cl$<br>C, 55.35 (55.42)<br>H, 5.62 (5.72)<br>N, 14.95 (14.91)<br>Cl, 12.47 (12.58) | 3280, 1705, 1670<br>1595, 1530, 1495 | (CDCl$_3$/CD$_3$OD = 3/1)<br>2.04(quint, J=7Hz, 2H), 2.61 (t, J=7Hz, 2H) 3.21–3.65(m, 4H), 3.86(t, J=7Hz, 2H), 6.57 7.13 ($A_2B_2$, J=9Hz, 4H), 8.70(br., 1H) |
| I a-38 | 98.5–99.5 (EtOH) | $C_{11}H_{16}N_4O_3$<br>C, 52.34 (52.37)<br>H, 6.38 (6.39)<br>N, 22.24 (22.21) | 3300, 1710, 1680<br>1630, 1540 | 2.02(quint, J=7Hz, 2H), 2.27(s, 3H), 2.59 (t, J=7Hz, 2H), 3.30–3.55(m, 4H), 3.83(t, J=7Hz, 2H), 5.47(s, 1H), 8.60(br., 1H) |
| I a-39 | 62.5–63.5 (Et$_2$O) | $C_{10}H_{14}N_4O_2$<br>C, 54.21 (54.04)<br>H, 6.38 (6.35)<br>N, 25.26 (25.21) | 3280, 1700,<br>1670 (sh), 1530 | 1.83–2.17(m, 2H), 2.57(t, J=7Hz, 2H), 3.75 (q, J=5Hz, 2H), 3.83(t, J=7Hz, 2H), 4.28 (t, J=5Hz, 2H), 6.23(d, J=2Hz, 1H), 7.37(d, J=2Hz, 1H), 7.53(d, J=2Hz, 1H), 8.53(br., 1H) |
| I a-40 | — | $C_{15}H_{21}N_3O_3$<br>C, 61.61 (61.84)<br>H, 7.22 (7.27)<br>N, 14.09 (14.42) | 1710, 1660, 1500<br>1470 (sh), 1455 | 1.92(quint, J=7Hz, 2H), 2.40(t, J=7Hz, 2H) 2.99(s, 3H), 3.26(t, J=6Hz, 2H), 3.50–3.80 (m, 4H), 3.72(s, 3H), 6.57, 6.76($A_2B_2$, J= 9Hz, 4H) |
| I a-41 | — | $C_{15}H_{26}H_2O_4$<br>C, 61.60 (61.63)<br>H, 6.97 (6.90)<br>N, 9.50 (9.58) | 1710, 1660, 1495<br>1470 (sh), 1455<br>1440 (sh), 1420 (sh) | 2.00(quint, J=7Hz, 2H), 2.42(t, J=7Hz, 2H) 3.10(s, 3H), 3.75(s, 3H), 3.60–3.80(m, 4H), 4.10(t, J=6Hz, 2H), 6.83(s, 4H) |

TABLE 5-continued

| Compd. No. | m.p. (°C.) (Recrystallizing Solvent) | Elementary Analysis Found (Calcd.) (%) | IR (cm$^{-1}$) (CHCl$_3$) | NMR (CDCl$_3$) δ |
|---|---|---|---|---|
| I a-42 | 62.5–64.5 (EtOH-Et$_2$O) | C$_{14}$H$_{18}$N$_2$O$_4$<br>C, 60.45 (60.42)<br>H, 6.55 (6.52)<br>N, 10.01 (10.07) | 3280, 1705, 1670 (sh), 1530, 1505, 1460 | 1.98(quint, J=7Hz, 2H), 2.55(t, J=7Hz, 2H) 3.75(s, 3H), 3.52–4.06(m, 6H) |
| I a-43 | — | C$_{19}$H$_{29}$N$_3$O$_3$<br>C, 65.46 (65.68)<br>H, 8.49 (8.41)<br>N, 11.95 (12.10) | 1705, 1650, 1500 1450, 1415 | 0.88(t, J=7Hz, 3H), 1.18(t, J=7Hz, 3H), 1.33–2.00(m, 4H), 2.30(t, J=7Hz, 2H), 3.00–3.55(m, 10H), 3.74(s, 3H), 6.65, 6.79(A$_2$B$_2$, J=9Hz, 4H) |

EXAMPLE 45

1-[2-[(4-Methoxyphenyl)allylamino]ethyl]carbamoyl]-2-oxopyrrolidine (Ia-44)

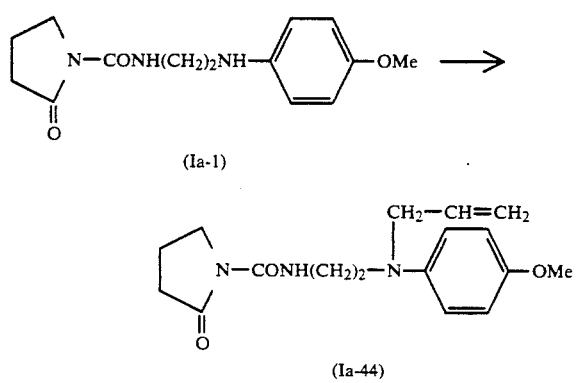

To a solution of 2.20 g (7.93 mmol) of 1-[2-[(4-methoxyphenylamino)ethyl]carbamoyl]-2-oxopyrrolidine (Ia-1) in 10 ml of DMA were added 1.01 ml (11.9 mmol) of allyl bromide and 1.92 ml (23.8 mmol) of pyridine, and the mixture was stirred for 20 min. at 80°–85° C. To the mixture were added 1.5 ml of pyridine and 0.8 ml of allyl bromide, and the mixture was further stirred for 10 min. and 1 hr. at the same temperature. The reaction solution was poured into ethyl acetate and washed with aqueous NaHCO$_3$, water, and saturated brine in order. After drying, the solvent was removed by evaporation. The residue was refined by silica gel column chromatography, and the resulting crystalline compound from the eluate with toluene-/ethyl acetate (8/1-3/1 v/v) was recrystallized from ether-n-hexane, whereby 1.92 g of the objective compound (Ia-44) melting at 53.0°–54.0° C. was obtained as crystals. Yield: 76.4%.

Anal. Calcd. (%) for C$_{17}$H$_{23}$N$_3$O$_3$: C, 64.33; H, 7.30; N, 13.24

Found (%): C, 64.13; H, 7.35; N, 13.35

IR (CHCl$_3$): 3310, 1705, 1675, 1540, 1505 cm$^{-1}$

NMR (CDCl$_3$): 1.83–2.17 (m, 2H), 2.57 (t, J=7 Hz, 2H) 3.40 (s, 4H), 3.73 (s, 3H), 3.80–3.90 (m, 4H), 5.05–5.25 (m, 2H), 5.60–6.05 (m, 1H), 6.80 (s, 4H), 8.52 (br., 1H)

EXAMPLE 46

1-[[2-(4-Methoxyphenylthio)ethyl]carbamoyl]-2-oxopyrrolidine (Ia-45)

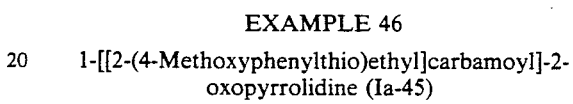

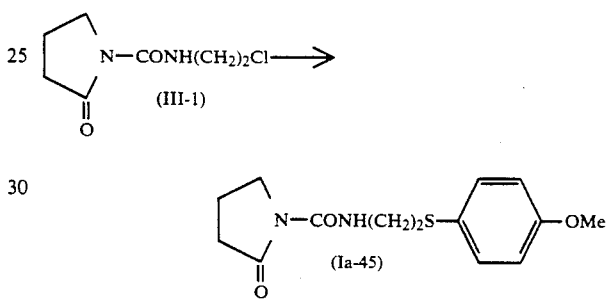

To a solution of 2.10 g (11.0 mmol) of 1-[2-chloroethylcarbamoyl]-2-oxopyrrolidine and 1.40 g (10 mmol) of 4-methoxybenzenethiol in 25 ml of DMF were added 2.47 g (16.5 mmol) of NaI and 3.02 g (22 mmol) of K$_2$CO$_3$, and the mixture was heated at 100° C. for 4.5 hr. The reaction solution was poured into ethyl acetate, washed with water, diluted hydrochloric acid, water, and saturated brine in order. After drying, the solvent was removed by evaporation. The residue was refined by silica gel column chromatography, whereby 2.78 g (94.6%) of the crystalline objective compound (Ia-45) was obtained from the eluate with benzene/ethyl acetate (8/1-5/1 v/v). The needles melting at 64.0°–65.0° C. are obtained by recrystallizing from ether-n-hexane. The properties of the objective compound (Ia-45) are shown in Table 7.

EXAMPLES 47–52

The reactions were carried out in the same method as in Example 46. The reaction conditions are shown in Table 6 and the properties are in Table 7.

TABLE 6

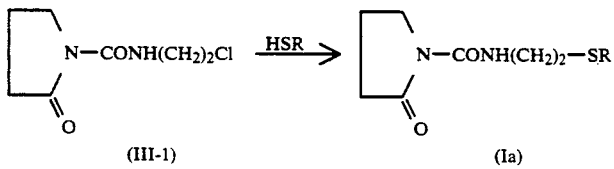

| | Compound (III-1) | HSR | K$_2$CO$_3$ | NaI | Reaction Conditions | Compound (Ia) |
|---|---|---|---|---|---|---|
| Ex | g | g | g | g | DMF Temp. (°C.) | Yield |

TABLE 6-continued

| No | (mmol) | R | (mmol) | (mmol) | (mmol) | (ml) | Time | (g) | (%) | No. |
|---|---|---|---|---|---|---|---|---|---|---|
| 47 | 3.50 (18.4) | 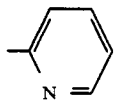 | 2.15 (19.3) | 5.05 (36.8) | 4.14 (27.6) | 40 | 110 21 hr. | 2.83 | 58.0 | Ia-46 |
| 48 | 2.50 (13.1) | 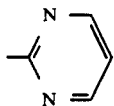 | 1.54 (13.8) | 3.6 (26.2) | 2.94 (19.6) | 25 | 100–105 89 hr. | 2.60 | 74.4 | Ia-47 |
| 49 | 2.50 (13.1) | 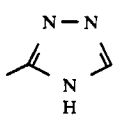 | 1.40 (13.8) | 3.6 (26.2) | 2.94 (19.6) | 25 | 105 89.5 hr. | 0.85 | 25.4 | Ia-48 |
| 50 | 1.09 (5.25) | 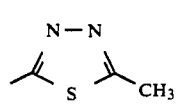 | 0.73 (5.51) | 1.44 (10.5) | 1.18 (7.88) | 20 | 110 3 hr. | 0.57 | 45.9 | Ia-49 |
| 51 | 3.50 (18.4) | 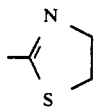 | 2.30 (19.3) | 5.05 (36.8) | 4.14 (27.6) | 40 | 110 14 hr. | 2.37 | 47.2 | Ia-50 |
| 52 | 3.50 (18.4) | 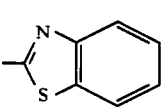 | 3.70 (22.1) | 5.05 (36.8) | 4.14 (27.6) | 40 | 110 14 hr. | 5.02 | 85.0 | Ia-51 |

TABLE 7

| Compd. No. | m.p. (°C.) (Recrystallizing Solvent) | Elementary Analysis Found (Calcd.) (%) | IR (CHCl$_3$) | NMR (CDCl$_3$) δ |
|---|---|---|---|---|
| I a-45 | 64.0–65.0 (Et$_2$O - n-hexane) | C$_{14}$H$_{18}$N$_2$O$_3$S C, 52.12 (57.12) H, 6.03 (6.16) N, 9.53 (9.52) S, 10.90 (10.89) | 3290, 1700, 1670 1585, 1530, 1485 1450, 1430 | 1.80–2.16(m, 2H), 2.57(t, J=7Hz, 2H), 2.97(t, J=7Hz, 2H), 3.45(q, 7Hz, 2H), 3.80(s, 3H), 3.82(t, J=7Hz, 2H), 6.85, 7.40(A$_2$B$_2$, J=9Hz, 4H), 8.67(br., 1H) |
| I a-46 | 62.5–63.5 (Et$_2$O) | C$_{12}$H$_{16}$N$_2$O$_2$S C, 54.39 (54.32) H, 5.70 (5.70) N, 15.83 (15.84) S, 11.96 (12.08) | 3300, 1700, 1675 1575, 1530, 1485 1450, 1405 | 1.83–2.18(m, 2H), 2.57(t, J=7Hz, 2H), 3.25–3.66(m, 4H), 3.83(t, J=7Hz, 2H), 6.85–7.60(m, 3H), 8.45(dd, J$_1$=6Hz, J$_2$=2Hz), 8.67(br., 1H) |
| I a-47 | 96.0–97.0 (EtOH) | C$_{11}$H$_{14}$N$_4$O$_2$S C, 49.60 (49.61) H, 5.33 (5.30) N, 20.97 (21.04) S, 11.94 (12.04) | 3300, 1700, 1670 1550 (sh), 1540 | 1.83–2.20(m, 2H), 2.58(t, J=7Hz, 2H), 3.33(t, J=7Hz, 2H), 3.62(q, J=7Hz, 2H), 3.84(t, J=7Hz, 2H), 6.97(t, J=5Hz, 1H), 8.55(d, J=5Hz, 2H), 8.70(br., 1H) |
| I a-48 | 123.0–124.0 (EtOH) | C$_9$H$_{13}$N$_5$O$_2$S C, 42.32 (42.24) H, 5.13 (5.13) N, 27.27 (27.43) S, 12.46 (12.56) | 3375, 3270, 1710 1675 | (CDCl$_3$.CDOD = 3/1) 1.86–2.20(m, 2H), 2.26(t, J=7H, 2H), 3.27(t, J=7Hz, 2H), 3.60(q, J=7Hz, 2H), 3.83(t, J=7Hz, 2H), 8.13(s, 1H), 8.77 (br. s, 1H) |
| I a-49 | 112.0–113.0 (EtOH) | C$_{10}$H$_{14}$N$_4$O$_2$S$_2$ C, 41.98 (41.94) H, 4.96 (4.93) N, 19.62 (19.56) S, 22.36 (22.39) | 3300, 1705, 1675 1530, 1480, 1450 1425, 1375 | 1.87–2.20(m, 2H), 2.59(t, J=7Hz, 2H), 2.71 (s, 3H), 3.40–3.95(m, 6H), 8.70(br., 1H) |
| I a-50 | 71.0–72.0 (EtOH) | C$_{10}$H$_{15}$N$_3$O$_2$S$_2$ C, 44.05 (43.94) H, 5.51 (5.53) N, 15.40 (15.37) S, 23.40 (23.46) | 3300, 1705, 1680 1560 (sh), 1530 1480, 1455, 1430 | 1.85–2.20(m, 2H), 2.60(t, J=7Hz, 2H), 3.19–3.47(m, 4H), 3.57(t, J=7Hz, 2H), 3.83 (t, J=7Hz, 2H), 4.20(t, J=7Hz, 2H), 8.63 (br., 1H) |
| I a-51 | 114.5–115.5 (EtOH) | C$_{14}$H$_{15}$N$_3$O$_2$S$_2$ C, 52.27 (52.32) H, 4.52 (4.70) N, 12.88 (13.07) S, 20.10 (19.95) | 3300, 1700, 1680 1530, 1480, 1455 1420 | 1.77–2.10(m, 2H), 2.48(t, J=7Hz, 2H), 3.45–3.78(m, 4H), 3.80(t, J=7Hz, 2H), 7.15–7.50(m, 2H), 7.67–7.90(m, 2H), 8.70 (br., 1H) |

EXAMPLE 53

1-[[2-(4-Methoxybenzenesulfonyl)ethyl]carbamoyl]-2-oxopyrrolidine (Ib-1)

The properties of the objective compound are shown in Table 10.

EXAMPLE 54

The reaction was carried out in the same method as in Example 53. The reaction conditions are shown in Table 8 and the properties are in Table 10.

TABLE 8

$$\underset{(Ia)}{\overset{O}{\underset{\|}{\text{N}}}-\text{CONH(CH}_2)_2-\text{S}-\text{R}} \longrightarrow \underset{(Ib)}{\overset{O}{\underset{\|}{\text{N}}}-\text{CONH(CH}_2)_2-\overset{(O)_2}{\underset{\|}{\text{S}}}-\text{R}}$$

| Ex. No. | Compound (Ia) R | mg (mmol) | CH$_2$Cl$_2$ (ml) | m-CPBA g (mmol) | Reaction Conditions Temp. (°C.) Time | Compound (Ib) Yield (g) (%) | Compound No. |
|---|---|---|---|---|---|---|---|
| 54 | 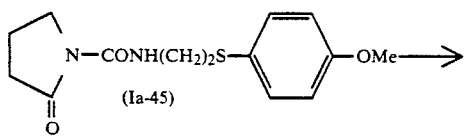 | 1.66 (6.23) | 55 | 2.70* (12.5) | Room Temp. 3 hr. | 1.10  59.1 | Ib-2 |

*Content 80%

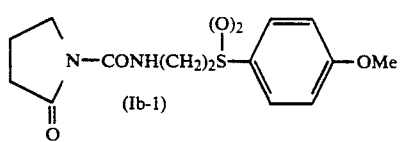

To a solution of 0.70 g (2.38 mmol) of 1-[[2-(4-methoxyphenylthio)ethyl]carbamoyl]-2-oxopyrrolidine in 30 ml of CH$_2$Cl$_2$ was added 0.96 g (4.76 mmol) of m-CPBA (content 85%), and the mixture was stirred for 1.5 hr. at room temperature. The reaction solution was poured into ethyl acetate, washed with aqueous NaHCO$_3$ and water. After drying, the solvent was removed by evaporation. The residue was refined by silica gel column chromatography, then the crystalline objective compound was obtained from the eluate with benzene/ethyl acetate (1/1 v/v). The product was recrystallized from ether to give 0.684 g of crystals (Ib-1) melting at 124.0°–125.0° C.

Yield: 88.0%

EXAMPLE 55

2-Oxo-1-[[2-(pyridin-2-ylsulfinyl)ethyl]carbamoyl]pyrrolidine (Ib-3)

To a solution of 2.0 g (7.54 mmol) of 2-oxo-1-[[2-(pyridin-2-ylthio)ethyl]carbamoyl]pyrrolidine in 35 ml of CH$_2$Cl$_2$ was added 1.63 g (7.54 mmol) of m-CPBA (content 80%) under ice-cooling. Then the mixture was stirred for 1.5 hr. at room temperature. The reaction solution was washed with aqueous NaHCO$_3$ and water. After drying, the solvent was removed by evaporration. The residue was refined by silica gel column chromatography, then the crystalline objective compound was obtained from the eluate with benzene/ethyl acetate (3/1-1/1 v/v). The compound was washed with Et$_2$O and collected by filtration, whereby 0.93 g of the crystalline compound (Ib-3) melting at 119.5°–120.5° C. was obtained. Yield: 43.9%.

The properties of the objective compounds are shown in Table 8.

EXAMPLES 56–57

In the same method as in Example 55, the reactions were carried out as shown in Table 9. The properties are shown in Table 10.

TABLE 9

$$\underset{\text{(Ia)}}{\begin{array}{c}\text{pyrrolidinone-}N-CONH(CH_2)_2-S-R\end{array}} \longrightarrow \underset{\text{(Ib)}}{\begin{array}{c}\text{pyrrolidinone-}N-CONH(CH_2)_2-\overset{O}{\underset{O}{S}}-R\end{array}}$$

| Ex. No. | Compound (Ia) R | mg (mmol) | CH$_2$Cl$_2$ (ml) | m-CPBA g (mmol) | Reaction Conditions Temp. (°C.) Time | Compound (Ib) Yield (g) | (%) | Compound No. |
|---|---|---|---|---|---|---|---|---|
| 56 | 2-pyrimidinyl | 1.62 (6.08) | 45 | 1.23* (6.08) | Room Temp. 2.25 hr. | 1.08 | 62.9 | Ib-4 |
| 57 | 2-benzothiazolyl | 2.13 (6.62) | 30 | 1.43** (6.62) | Room Temp. 2.5 hr. | 1.86 | 83.2 | Ib-5 |

*Content 85%;
**Content 80%

TABLE 10

| Compd. No. | m.p. (°C.) (Recrystallizing Solvent) | Elementary Analysis Found (Calcd.) (%) | IR (cm$^{-1}$) (CHCl$_3$) | NMR (CDCl$_3$) δ |
|---|---|---|---|---|
| I b-1 | 124.0–125.0 (EtOH) | C$_{14}$H$_{18}$N$_2$O$_6$S<br>C, 51.48 (51.52)<br>H, 5.52 (5.56)<br>N, 8.64 (8.58)<br>S, 9.87 (9.82) | 3300, 1710, 1685<br>1595, 1580, 1535<br>1500 | 1.80–2.15(m, 2H), 2.56(t, J=7Hz, 2H), 3.37 (t, J=6Hz, 2H), 3.62(q, J=6Hz, 2H), 3.74 (t, J=7Hz, 2H), 3.88(s, 3H), 7.02, 7.84 (A$_2$B$_2$, J=9Hz, 4H), 8.64(br. s, 1H) |
| I b-2 | 104.5–105.5 (EtOH) | C$_{11}$H$_{14}$N$_4$O$_4$S<br>C, 44.25 (44.29)<br>H, 4.70 (4.73)<br>N, 18.74 (18.78)<br>S, 10.63 (10.75) | 3300, 1710, 1685<br>1560, 1535, 1485<br>1460, 1430 | 1.85–2.18(m, 2H), 2.57(t, J=7Hz, 2H),<br>3.73–3.90(m, 6H), 7.58(t, J=5Hz, 1H),<br>8.98(d, J=5Hz, 2H), 8.74(br., 1H) |
| I b-3 | 119.5–120.5 (Et$_2$O) | C$_{12}$H$_{15}$N$_3$O$_3$S<br>C, 51.18 (51.23)<br>H, 5.26 (5.37)<br>N, 14.87 (14.94)<br>S, 11.47 (11.40) | 3290, 1710, 1680<br>1575, 1530 | 1.80–2.16(m, 2H), 2.56(t, J=7Hz, 2H),<br>3.02–3.41(m, 2H), 3.55–3.87(m, 4H),<br>7.27–7.45(m, 1H), 7.80–8.07(m, 2H),<br>8.50–8.75(m, 2H) |
| I b-4 | 123.0–124.0 (EtOH) | C$_{11}$H$_{14}$N$_4$O$_3$S<br>C, 46.83 (46.80)<br>H, 5.06 (5.00)<br>N, 19.71 (19.85)<br>S, 11.08 (11.36) | 3290, 1710, 1685<br>1560, 1530 | 1.84–2.19(m, 2H), 2.57(t, J=7Hz, 2H),<br>3.23–3.50(m, 2H), 3.66–3.88(m, 4H), 7.43 (t, J=6Hz, 1H), 8.57(br., 1H), 8.90(d, J=6Hz, 2H) |
| I b-5 | 144.0–145.0 (EtOH) | C$_{14}$H$_{15}$N$_3$O$_2$S$_2$<br>C, 49.86 (49.84)<br>H, 4.35 (4.48)<br>N, 12.39 (12.45)<br>S, 18.87 (19.00) | 3280, 1710, 1685<br>1525 | 1.70–2.00(m, 2H), 2.27–2.50(m, 2H), 3.50–3.95(m, 6H), 7.37–7.66(m, 2H), 7.95–8.14 (m, 2H), 8.53(br., 1H) |

EXAMPLES 58–65

The reactions were carried out in the same method as in the aforementioned Example 1, whereby the compounds (Ia) were obtained. The reaction conditions and the properties of thee objective compounds are shown in Tables 11 and 12, respectively.

TABLE 11

$$\text{(III-2)} \quad \underset{\text{N—CONH(CH}_2)_3\text{Cl}}{\overset{\text{O}}{\bigcirc}} \xrightarrow[\text{Z}^2]{\text{HN}\overset{Z_1}{\underset{Z^2}{\diagup}} \text{(V)}} \quad \underset{\text{N—CONH(CH}_2)_3\text{N}\overset{Z^1}{\underset{Z^2}{\diagup}}}{\overset{\text{O}}{\bigcirc}} \quad \text{(Ia)}$$

| Ex. No. | Compound (III-2) g (mmol) | (V) g (mmol) | K₂CO₃ g (mmol) | NaI g (mmol) | DMF (ml) | Reaction Condition Temp. (°C.) Time | Compound (Ia) Z¹, | Z² | Yield (g) | (%) | Compd. No. |
|---|---|---|---|---|---|---|---|---|---|---|---|
| 58 | 3.17 (15.5) | 2.10 (17.0) | 5.36 (38.8) | 3.48 (23.2) | 35 | 105–110 29 hr. | 4-MeO-C₆H₄- | H | 1.90 | 42.1 | Ia-52 |
| 59 | 3.00 (14.7) | 3.41 (16.1) | 5.08 (36.8) | 3.30 (22.1) | 35 | 100–105 6 d. | piperidinyl with 4-Cl-C₆H₄ and OH | | 4.24 | 76.0 | Ia-53 |
| 60 | 3.00 (14.7) | 2.84 (16.1) | 5.08 (36.8) | 3.30 (22.1) | 35 | 100–105 6 d. | piperidinyl-NCH₂Ph | | 4.29 | 85.0 | Ia-54 |
| 61 | 2.74 (13.4) | 2.50 (14.1) | 4.63 (33.5) | 3.0 (20.1) | 30 | 100–105 3 d. | piperidinyl with C₆H₅ and OH | | 3.95 | 85.4 | Ia-55 |
| 62 | 1.23 (6.0) | 1.27 (6.12) | 2.07 (15.0) | 1.35 (9.0) | 20 | 95–100 4 d. | piperidinyl with 4-MeO-C₆H₄ and OH | | 1.49 | 66.0 | Ia-56 |
| 63 | 3.73 (18.2) | 3.34 (18.2) | 7.55 (54.6) | 4.06 (27.3) | 35 | 100–105 4 d. | piperidinyl with thienyl and OH | | 5.76 | 89.9 | Ia-57 |
| 64 | 2.08 (10.9) | 2.14 (11.6) | 4.52 (32.7) | 2.45 (16.4) | 30 | 100–105 4 d. | piperidinyl with thienyl and OH | | 3.12 | 81.5 | Ia-58 |
| 65 | 2.99 (14.6) | 3.10 (14.6) | 6.05 (43.8) | 3.28 (21.9) | 35 | 100–105 5 d. | piperidinyl with 4-Cl-C₆H₄ and OH | | 4.96 | 89.3 | Ia-59 |

TABLE 12

| Compound No. | m.p. (°C.) (Recrystallizing Solvent) | Elementary Analysis Found (Calcd.) (%) | IR (cm⁻¹) | NMR (CDCl₃) δ |
|---|---|---|---|---|
| I a-52 | 114.5–115.5 (EtOH) | $C_{16}H_{21}N_3O_3$<br>C, 61.78 (61.84)<br>H, 7.13 (7.26)<br>N, 14.36 (14.42) | (CHCl₃)<br>3280, 1700, 1670<br>1540, 1500, 1480<br>1455 | 1.83(t, J=6Hz, 2H), 2.01(quint, J=7Hz, 2H)<br>2.60(t, J=7Hz, 2H), 3.16(t, J=6Hz, 2H),<br>3.45(q, J=6Hz, 2H), 3.75(s, 3H), 3.86(t,<br>J=7Hz, 2H), 6.60, 6.80(A₂B₂, J=9Hz, 4H),<br>8.50(br., 1H) |
| I a-53 | 138.0–139.0 (EtOH—Et₂O) | $C_{19}H_{26}N_3O_3Cl$<br>C, 59.73 (60.07)<br>H, 6.92 (6.90)<br>N, 10.93 (11.06)<br>Cl, 9.55 (9.33) | (CHCl₃)<br>3290, 1700, 1670<br>1535, 1480 | 1.60–3.40(m, 16H), 3.36(q, J=6Hz, 2H),<br>3.77(t, J=7Hz, 2H), 7.30, 7.47(A₂B₂, J=9Hz<br>4H), 8.58(br., 1H) |
| I a-54 | dimaleate 200.0–201.0 (d) (MeOH-i-PrOH) | $C_{19}H_{28}N_4O_2\cdot 2C_4H_4O_4$<br>C, 56.02 (56.24)<br>H, 6.28 (6.29)<br>N, 9.75 (9.72) | (Nujol) dimaleate<br>3250, 1700<br>1680 (sh), 1610<br>1560 | (CD₃OD: D₂O = 6:1) dimaleate<br>1.78–2.03(m, 4H), 2.54(t, J=7Hz, 2H),<br>3.03–3.93(m, 12H), 3.68(t, J=7Hz, 2H),<br>4.19(s, 2H), 6.21(s, 4H), 7.42(s, 5H) |
| I a-55 | 94.5–95.5 (i-PrOH-Et₂O) | $C_{19}H_{27}N_3O_3$<br>C, 66.13 (66.06)<br>H, 7.84 (7.88)<br>N, 12.14 (12.17) | (CHCl₃)<br>3295, 2920, 2800<br>1705, 1670, 1535 | 1.70–2.88(m, 17H), 3.37(q, J=6Hz, 2H)<br>3.85(t, J=7Hz, 2H), 7.20–7.60(m, 5H), 8.57<br>(br., 1H) |
| I a-56 | 98.5–99.0 (i-PrOH-Et₂O) | $C_{20}H_{29}N_3O_4$<br>C, 63.69 (63.97)<br>H, 7.83 (7.79)<br>N, 11.20 (11.19) | (CHCl₃)<br>3275, 2920, 1705<br>1603, 1535, 1505 | 1.60–2.90(m, 17H), 3.36(q, J=6Hz, 2H)<br>3.79(s, 3H), 3.83(t, J=7Hz, 2H), 6.86,<br>7.44(A₂B₂, J=9Hz, 4H), 8.55(br., 1H) |
| I a-57 | ½(COOH)₂ 224.0–226.0 (d) (MeOH-i-PrOH) | $C_{17}H_{25}N_3O_3S\cdot CHO_2$<br>C, 54.42 (54.81)<br>H, 6.51 (6.64)<br>N, 10.56 (10.65)<br>S, 7.93 (8.13) | (Nujol)<br>½(COOH)₂<br>3290, 3110, 1700<br>1678, 1630 | (free base)<br>1.744(quint, J=7.2Hz, 17H), 1.85–2.25(m,<br>6H), 2.40–2.80(m, 8H), 3.346(q, J=6Hz,<br>2H), 3.83(t, J=7Hz, 2H), 6.97–6.98(m, 2H),<br>7.17–7.21(m, 1H), 8.516(br., 1H) |
| I a-58 | (COOH)₂ 144.0–145.0 (i-PrOH) | $C_{17}H_{25}N_3O_3S\cdot C_2H_2O_4\cdot\tfrac{1}{2}H_2O$<br>C, 50.86 (50.66)<br>H, 6.08 (6.26)<br>N, 9.26 (9.33)<br>S, 7.12 (7.12) | (Nujol)<br>(COOH)₂<br>3450, 3310, 3230<br>1700, 1665, 1640<br>1620 (sh) | (free base)<br>1.65–1.85(m, 4H), 1.90–2.10(m, 5H), 2.240,<br>2.879(ABq, J=11Hz, 2H), 2.469(t, J=7Hz,<br>2H), 2.613(t, J=8Hz, 2H), 2.937(br.,<br>J=12Hz, 1H), 3.900(m, 2H), 3.865(t, J=7Hz,<br>2H), 4.230(br. s, 1H), 6.956–6.974(m,<br>2H), 7.187–7.273(m, 1H), 8.607(br. s, 1H) |
| I a-59 | 74.5–76.0 (Et₂O) | $C_{19}H_{26}N_3O_3Cl$<br>C, 60.16 (60.07)<br>H, 6.72 (6.90)<br>N, 11.12 (11.06)<br>S, 9.40 (9.33) | (CHCl₃)<br>3470, 3300, 1705<br>1670, 1540, 1485 | 1.65–1.82(m, 5H), 1.90–2.10(m, 4H), 2.198<br>(a part of ABq, J=11Hz, 1H), 2.467(t,<br>J=5Hz, 2H), 4.16(s, 1H), 7.26–7.50(m, 4H),<br>8.594(br. s, 1H) |

EXAMPLE 66

1-[[3-(4-Phenyl-1,2,3,6-tetrahydropyridin-1-yl)propyl]-carbamoyl]-2-oxopyrrolidine maleate (Ic-1)

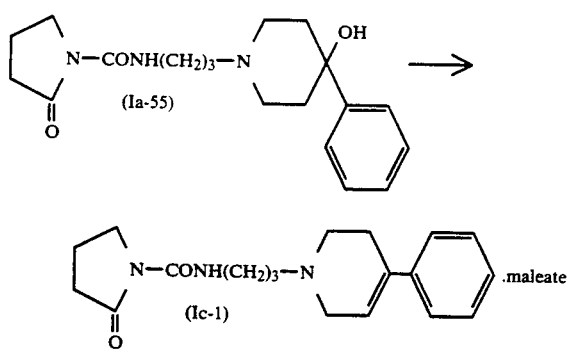

A solution of 1.67 g (4.83 mmol) of 1-[[3-(4-hydroxy-4-phenyl-1-piperidino)propyl]carbamoyl]-2-oxopyrrolidine (Ia-55) in 25 ml of 10% hydrochloric acid was refluxed for 2 hr. The reaction solution was made alkaline with aqueous NaHCO₃, extracted with ethyl acetate, and washed with saturated brine. After drying, the solvent was removed by evaporation. The residue was refined by silica gel column chromatography, whereby 0.65 g of the objective product (Ic-1) was obtained from the eluate with ethyl acetate. Yield: 41%.

The objective product (Ic-1) (maleate) was recrystallized from isopropyl alcohol-ether, whereby crystals melting at 145.0°–148° C. were obtained.

The properties of the objective compound (Ic-1) are shown in Table 13.

EXAMPLE 67

1-[[3-[4-(4-Chlorophenyl)-1,2,3,6-tetrahydropyridin-1-yl]propyl]carbamoyl]-2-oxopyrrolidine (Ic-2)

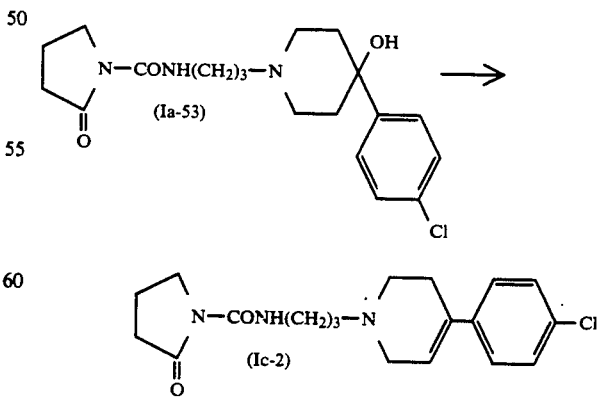

A solution of 1.6 g (4.21 mmol) of 1-[[3-[4-(4-chlorophenyl)-4-hydroxypiperidin-1-yl]propyl]carbamoyl]-2oxopyrrolidine (Ia-53) and 0.96 g (5.05 mmol) of p-toluenesulfonic acid monohydrate in 75 ml of toluene was refluxed for 29 hr. The water was removed azeotropically using a Dean-Stark trap containing 10 g of Molecular Sieves-4A. The solution, after being made alkaline with aqueous NaOH, was extracted with ethyl acetate, and the organic layer was washed with water and saturated brine in order. After drying, the solvent was removed by evaporation. The residue was refined by silica gel column chromatography, whereby 1.50 g of the objective crystalline compound (Ic-2) was obtained from the eluate with ethyl acetate and then $CH_2Cl_2$/MeOH (20/1 v/v).

Yield: 98.4%.

By recrystallizing from ether-isopropyl alcohol, crystals melting at 88.0°–88.5° C. were obtained. The properties of the objective compound (Ic-2) are shown in Table 13.

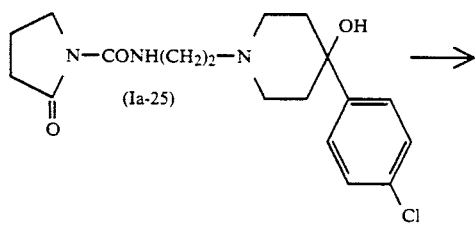

(Ia-29)

A solution of 1.68 g (4.59 mmol) of 1-[[2-[4-(4-chlorophenyl)-4-hydroxypiperidin-1-yl]ethyl]carbamoyl]-2-oxopyrrolidine (Ia-25) and 1.05 g (5.5 mmol) of p-toluenesulfonic acid monohydrate in 75 ml of toluene was refluxed for 25 hr. using a Dean-Stark trap containing 10 g of Molecular Sieves-4A. By proceeding as in Example 67, 1.57 g of the objective compound (Ia-29) was obtained.

TABLE 13

| Compd. No. | m.p. (°C.) (Recrystallizing Solvent) | Elementary Analysis Found (Calcd.) (%) | IR (cm$^{-1}$) | NMR δ |
|---|---|---|---|---|
| I c-1 | maleate 145.0–148.0 (i-PrOH-Et$_2$O) | $C_{19}H_{25}N_3O_2$· $C_4H_4O_4$ C, 62.35 (62.29) H, 6.62 (6.59) N, 9.46 (9.48) | (Nujol) maleate 3300, 2910, 2840 1705, 1675, 1620 1580, 1510 | (CD$_3$OD) maleate 1.95–2.15(m, 4H), 2.61(t. J=8Hz, 2H), 2.90(br., 2H), 3.25–3.35(m, 2H), 3.43 (t, J=6Hz, 2H), 3.58(br., 2H), 3.81(t, t=7Hz, 2H), 3.96(br., 2H), 6.15(br., 1H), 6.25(s, 2H), 7.30–7.55(m, 5H) |
| I c-2 | 88.0–88.5 (i-PrOH-Et$_2$O) | $C_{19}H_{24}N_3O_2Cl$ C, 63.16 (63.06) H, 6.74 (6.68) N, 11.61 (11.61) Cl, 10.02 (9.80) | (CHCl$_3$) 3275, 2850, 1705 1530 | (CDCl$_3$) 1.75–1.90(m, 2H), 2.02(quint, J=7Hz, 2H), 2.47–2.75(m, 8H), 3.16(q, J=3Hz, 2H), 3.38(q, J=6Hz, 2H), 3.86(t, J=7Hz, 2H), 6.05(br., 1H), 7.27, 7.30(A$_2$B$_2$, J=7Hz, 4H) 8.48(br., 1H) |

EXAMPLE 68

1-[[2-[4-(4-Chlorophenyl)-1,2,3,6-tetrahydropyridin-1-yl]ethyl]carbamoyl]-2-oxopyrrolidine (Ia-29)

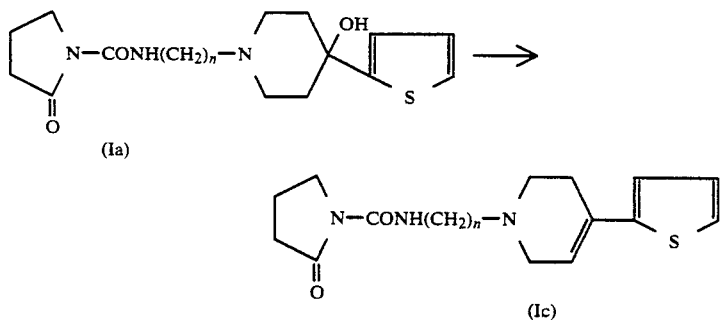

Yield: 98.3%

EXAMPLES 69–72

In the same method as in Example 68, the reactions were carried out under the conditions shown in Tables 14 and 15, whereby the objective compounds (Ic) were obtained. The properties are shown in Table 16.

TABLE 14

| Ex. No. | Compd. (Ia) n | Compd. (Ia) g (mmol) | p-TsOH·H$_2$O g (mmol) | Toluene (ml) | Refluxing Time (hr.) | Compound (Ic) Yield (g) | Compound (Ic) Yield (%) | Compound (Ic) No. |
|---|---|---|---|---|---|---|---|---|
| 69 | 3 | 4.23 (12.0) | 2.75 (14.4) | 250 | 26 | 3.94 | 98.2 | Ic-3 |
| 70 | 2 | 2.00 (5.93) | 1.46 (7.70) | 150 | 25 | 1.75 | 92.4 | Ic-4 |

TABLE 15

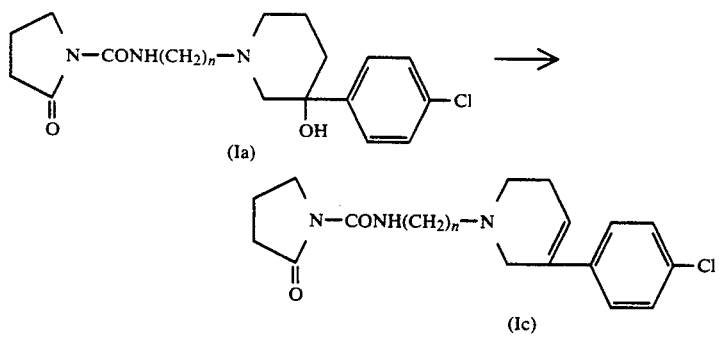

| Ex. No. | Compd. (Ia) n | g (mmol) | p-TsOH.H2O g (mmol) | Toluene (ml) | Refluxing Time (hr.) | Compound (Ic) Yield (g) | (%) | No. |
|---|---|---|---|---|---|---|---|---|
| 71 | 3 | 4.40 (11.6) | 2.97 (15.6) | 250 | 48 | 3.57 | 85.0 | Ic-5 |
| 72 | 2 | 1.60 (4.37) | 1.12 (5.90) | 120 | 48 | 1.52 | 92.1 | Ic-6 |

TABLE 16

| Compd. No. | m.p. (°C.) (Recrystallizing Solvent) | Elementary Analysis Found (Calcd.) (%) | IR (cm$^{-1}$) (CHCl$_3$) | NMR (CDCl$_3$) δ |
|---|---|---|---|---|
| I c-3 | maleate 152.0–153.5 (MeOH-i-PrOH) | C$_{17}$H$_{23}$N$_3$O$_2$S .C$_4$H$_4$O$_4$<br>C, 56.06 (56.11)<br>H, 5.95 (6.05)<br>N, 9.41 (9.35)<br>S, 7.04 (7.13) | (Nujol) maleate 3320, 1715, 1690 1620, 1595, 1530 | (free base) 1.804(quint, J=7Hz, 2H), 2.015(quint, J=7Hz, 2H) 2.50–2.75(m, 8H), 3.131(quint, J=3Hz, 2H), 3.380(q, J=6Hz, 2H), 3.855 (t, J=7Hz, 2H), 6.075(m, 1H), 6.90–7.30 (m, 3H), 8.499(br., 1H) |
| I c-4 | 98.5–100 (i-PrOH-Et$_2$O) | C$_{16}$H$_{21}$N$_3$O$_2$S<br>C, 60.26 (60.16)<br>H, 6.62 (6.63)<br>N, 13.09 (13.16)<br>S, 9.88 (10.04) | 3300, 1730, 1675 1540 | 2.022(quint, J=7.2Hz. 2H), 2.55–2.80(m, 8H), 3.194(q, J=3Hz, 2H), 3.489(q, J=6Hz, 2H), 3.858(t, J=7Hz, 2H), 6.071(m, 1H), 6.90–7.15(m, 3H), 8.613(br., 1H) |
| I c-5 | maleate 134.5–135.5 (i-PrOH) | C$_{19}$H$_{24}$N$_3$O$_2$Cl .C$_4$H$_4$O$_4$1/5H$_2$O<br>C, 57.46 (57.37)<br>H, 5.82 (5.94)<br>N, 8.56 (8.73)<br>Cl, 7.29 (7.36) | (Nujol) maleate 3290, 1695, 1610 1570 (sh), 1525 1450 | (free base) 1.845(quint, J=7Hz, 2H), 2.014(quint, J=7Hz, 2H), 2.30–2.40(m, 2H), 2.55–2.65 m, 6H), 3.27–3.30(m. 2H), 3.392(q, J=6Hz, 2H), 3.854(t, J=7Hz, 2H), 6.09–6.12(m, 1H), 7.264(s, 4H), 8.499(br. s, 1H) |
| I c-6 | 102.5–104.0 (MeOH-Et$_2$O) | C$_{18}$H$_{22}$N$_3$O$_2$Cl<br>C, 62.10 (62.15)<br>H, 6.35 (6.37)<br>N, 11.91 (12.08)<br>Cl, 9.99 (10.19) | 3290, 1705, 1670 1540, 1520 (sh), 1485 | 2.026(quint, J=7Hz, 2H), 2.343–2.380 (m, 2H), 2.558–2.757(m, 6H), 3.357(s, 2H), 3.527(q, J=5.6Hz, 2H), 3.864(t, J=7Hz, 2H), 6.10–6.15(m, 1H), 7.265(s, 4H), 8.624(br. s, 1H) |

REFERENTIAL EXAMPLE 1

2-Oxo-1-phenoxycarbonylpyrrolidine

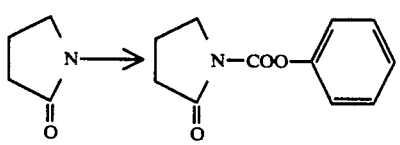
(II)

To a solution of 7.36 g (184 mmol) of NaH (60%) in 200 ml of THF was added 15.68 g (184 mmol) of 2-oxopyrrolidine with stirring under ice-cooling, and further the mixture was stirred at room temperature for 1 hr. until H$_2$ gas ceased to evolve. The reaction solution was added to a solution of 29.7 g (190 mmol) of phenyl chloroformate in 100 ml of THF cooled at −60° C. and then stirred at room temperature for 4 hr. The reaction solution was poured into ice water, and then extracted with ethyl acetate. After drying, the solvent was removed by evaporation. When the crystalline residue was recrystallized from CH$_2$Cl$_2$-ether, 37.8 g of the objective compound (II) melting at 120.0°–121.5° C. was obtained as crystals. Yield: 84.0%.

The properties of the objective compound are shown in Table 17.

REFERENTIAL EXAMPLE 2

1-(2-Chloroethylcarbamoyl)-2-oxopyrrolidine (III-1)

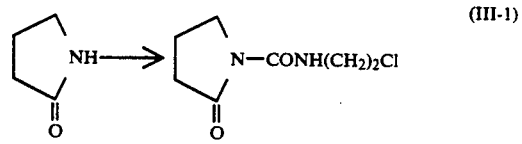
(III-1)

A mixture of 65.1 g (765 mmol) of 2-oxopyrrolidine and 67.3 g (638 mmol) of chloroethyl isocyanate was heated with stirring at 95°–105° C. overnight. After cooling, the reaction solution was refined by silica gel chromatography. The resulting compound obtained from the eluate with toluene-ethyl acetate (20/1-10/1 v/v) was recrystallized from $CH_2Cl_2$-ether-n-hexane, whereby 107.7 g of the objective compound 1-(2-chloroethylcarbamoyl)-2-oxopyrrolidine (III-1) melting at 66.5°-67.5° C. was obtained as crystals.

Yield: 88.5%.

The properties of the objective compound are shown in Table 17.

REFERENTIAL EXAMPLE 3

1-(3-Chloropropylcarbamoyl)-2-oxopyrrolidine (III-2)

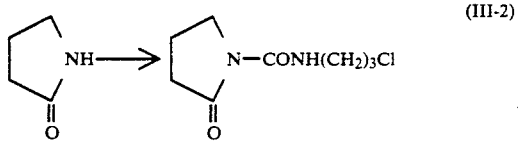

(III-2)

A mixture of 17.1 g (201 mmol) of 2-oxopyrrolidine and 20 g (167 mmol) of chloropropyl isocyanate was heated with stirring at 95°-105° C. overnight. After cooling, the reaction resolution was refined by silica gel chromatography. The resulting product obtained from the eluate with toluene-ethyl acetate (20/1-10/1 v/v) was washed with ether-n-hexane and then collected by filtration, whereby 27.87 g of the objective compound 1-(3-chloropropylcarbamoyl)-2-oxopyrrolidine (III-2) melting at 57.0°-58.0° C. was obtained as crystals. Yield: 81.0%.

The properties of the objective compound are shown in Table 17.

EXPERIMENT

Prevention against the ECS-Induced Amnesia in Mice

The test apparatus was a black acrylic resin box (30×30×30 cm) with an electrifiable grid floor in which a white wooden platform (10×10×1 cm) was placed in one corner. The step-down passive avoidance test was conducted on 3 groups of 10 SD mice each (male, 4 to 5 weeks age). A solvent was orally administered to the animals of the first group as a control group and the test compounds at doses of 5 and 50 mg/kg were orally given to other 2 groups 60 min. before the acquisition trial. In the acquisition trail, mice were individually placed on the platform and a scrambled foot shock (3 mA, for 5 sec.) was delivered through the grid floor as soon as the mouse moved off the platform. five to ten min. after the foot shock, a single electroconductive shock (30 mA, 100 Hz (rectangular wave), for 0.2 sec.) was administered transcorneally and then each animal was placed in the home cage. After 24 hr. later, each mouse was again placed on the platform and the latency for descending on the grid floor was measured. a long latency in the retention test indicates good acquisition. The step-down latencies were evaluated using the Mann-Whitney U-test.

In Table 5, the results were shown as percent change in latencies over control defined as 100.

TABLE 5

Effects of Compounds against Amnesia Induced by Electro Convulsive Shock

| Compound No. | 5 mg/kg | 50 mg/kg |
|---|---|---|

TABLE 17

| Ref. Ex. No. | m.p. (°C.) (Recrystallizing Solvent) | Elementary Analysis Found (Calcd.) (%) | IR (cm$^{-1}$) (CHCl$_3$) | NMR (CDCl$_3$) δ |
|---|---|---|---|---|
| 1 | 120.0-121.5 (CH$_2$Cl$_2$-Et$_2$O) | C$_{11}$H$_{11}$NO$_3$<br>C, 64.43 (64.38)<br>H, 5.33 (5.40)<br>N, 6.87 (6.83) | 1795, 1750 (sh),<br>1730, 1590, 1485 | 2.09(quint, J=7Hz, 2H), 2.60(t, J=7Hz, 2H)<br>3.93(t, J=7Hz, 2H), 7.10-7.50(m, 5H) |
| 2 | 66.5-67.5 (CH$_2$Cl$_2$-Et$_2$O-n-hexane) | C$_7$H$_{11}$N$_2$O$_2$Cl<br>C, 43.83 (44.10)<br>H, 5.80 (5.82)<br>N, 14.88 (14.70)<br>Cl, 18.80 (18.60) | 3300, 1705, 1680<br>1540 | 2.04(quint, J=7Hz, 2H), 2.63(t, J=7Hz, 2H)<br>3.63(s, 2H), 3.66(s, 2H), 3.87(t, J=7Hz, 2H), 8.77(br. s, 1H) |
| 3 | 57.0-58.0 (Et$_2$O-n-hexane) | C$_8$H$_{13}$N$_2$O$_2$Cl<br>C, 46.96 (46.95)<br>H, 6.37 (6.40)<br>N, 13.78 (13.69)<br>Cl, 17.48 (17.32) | 3275, 1700,<br>1670 (sh), 1530, | 1.80-2.20(m, 4H), 2.60(t, J=7Hz, 2H), 3.45 (q, J=6Hz, 2H), 3.84(t, J=6Hz, 2H), 8.46 (br. s, 1H) |

PREPARATION

| | |
|---|---|
| 1-[[2-(4-Methoxyphenyl)aminoethyl]-carbamoyl]-2-oxopyrrolidine | 10 mg |
| Wheat starch | 48 mg |
| Magnesium stearate | 2 mg |

The above ingredients are admixed each other to prepare a capsule.

EFFECT OF THE INVENTION

Carbamoylpyrrolidone derivatives (I) of the present invention showed good activity against amnesia introduced by electro convulsive shock.

In the following experiment of the compounds of this invention, the numberes of the test compounds correspond to them in Examples and/or Tables.

| | | |
|---|---|---|
| I a - 1 | 302*** | 219* |
| I a - 5 | 166** | 108 |
| I a - 18 | 223* | 249** |
| I a - 25 | 222*** | 205*** |
| I a - 45 | 144 | 181*** |
| I a - 53 | 181** | 122 |

*p <0.05
**p <0.025
***p <0.01

What we claim is:

1. A compound of the formula:

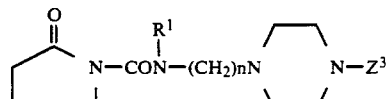

wherein $R^1$ is hydrogen, or $C_1$-$C_6$ alkyl; n is an integer from 2 to 3; $Z^3$ is hydroxyethyl, dimethylsulfamoyl, pyrimidinyl, pyridyl, benzyl, benzyl substituted by halogen, methyl or methoxy, phenyl, phenyl substituted by halogen, methyl or methoxy, phenylsulfonyl or phenylsulfonyl substituted by halogen, methyl or methoxy; or a pharmaceutically acceptable acid addition salt thereof.

2. A compound as claimed in claim 1, which is 1-[2-[4-(pyrimidin-2-yl)-1-piperazinyl]ethylcarbamoyl]-2-oxopyrrolidine.

3. A pharmaceutical composition comprising a pharmacologically effective amount of a compound as recited in claim 1, together with a carrier, diluent, or excipient.

* * * * *